(12) United States Patent
Takahashi et al.

(10) Patent No.: US 8,193,146 B2
(45) Date of Patent: Jun. 5, 2012

(54) METHOD OF AMELIORATING SYMPTOM CAUSED BY MOOD DISTURBANCE

(75) Inventors: Yasuhiko Takahashi, Toyonaka (JP); Kenji Oeda, Kyoto (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/908,912

(22) PCT Filed: Mar. 15, 2006

(86) PCT No.: PCT/JP2006/305633
§ 371 (c)(1),
(2), (4) Date: Dec. 10, 2008

(87) PCT Pub. No.: WO2006/098488
PCT Pub. Date: Sep. 21, 2006

(65) Prior Publication Data
US 2009/0210949 A1    Aug. 20, 2009

(30) Foreign Application Priority Data

Mar. 15, 2005   (JP) ................................. 2005-072849

(51) Int. Cl.
*A61K 38/00*    (2006.01)
*A61K 48/00*    (2006.01)
(52) U.S. Cl. ...................................... 514/1.1; 514/44 R
(58) Field of Classification Search .................. 514/1.1, 514/44 R
See application file for complete search history.

(56) References Cited

U.S. PATENT DOCUMENTS

| 6,420,388 B1 | 7/2002 | Emonds-Alt et al. |
| 2005/0260595 A1 * | 11/2005 | Takahashi et al. ................ 435/6 |

FOREIGN PATENT DOCUMENTS

| EP | 1 382 613 A1 | 1/2004 |
| JP | 2000-316583 A | 11/2000 |
| JP | 2004-350672 A | 12/2004 |
| WO | 0061125 A2 | 10/2000 |
| WO | 2005047318 A1 | 5/2005 |

OTHER PUBLICATIONS

Printout from http://www.nimh.nih.gov/health/topics/anxiety-disorders/index.shtml, printed Jan. 8, 2010, p. 1.*
Int'l Search Report issued May 23, 2006 in Int'l Application No. PCT/JP2006/305633.
Int'l Preliminary Report on Patentability Aug. 12, 2008 in Int'l Application No. PCT/JP2006/305633.
EP Search Report issued Jul. 21, 2008 in EP Application No. 06729600.4.
Office Action issued Feb. 4, 2011 in EP Application No. 06729600.4.
Zigman et al, "Human Golfalpha: Complementary Deoxyribonucleic Acid Structure and Expression in Pancreatic Islets and Other Tissues Outside the Olfactory Neuroepithelium and Central Nervous System," Endocrinology, vol. 133, No. 6, pp. 2508-2514 (1993).
Hamamura et al, "Elucidation of Action Mechanism of Antidepressants in Brain—In focus on Golf protein expressed specifically in nucleus accumbens of the striatum," Seishin Yakuryo Kenkyu Nenpo, vol. 35, pp. 203-208 (2003).
Chen et al, "Regulation of Signal Transduction Pathways and Gene Expression by Mood Stabilizers and Antidepressants," Psychosomatic Medicine, vol. 61, pp. 599-617 (1999).

* cited by examiner

*Primary Examiner* — Marcia S Noble
(74) *Attorney, Agent, or Firm* — Panitch Schwarze Belisario & Nadel LLP

(57) ABSTRACT

The present invention relates to a method for improving symptom of mood disorder or its related disorder comprising a step of allowing Gm1 protein and the like to be excessively present in a brain of a mammal, and a non-human mammal, to which the method has been applied, and the like.

2 Claims, 1 Drawing Sheet

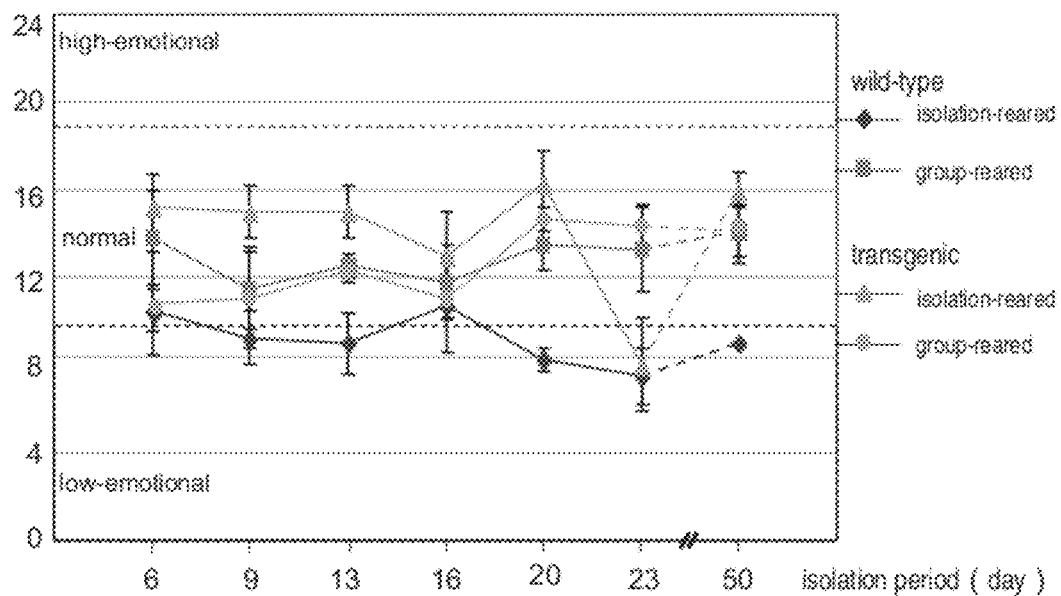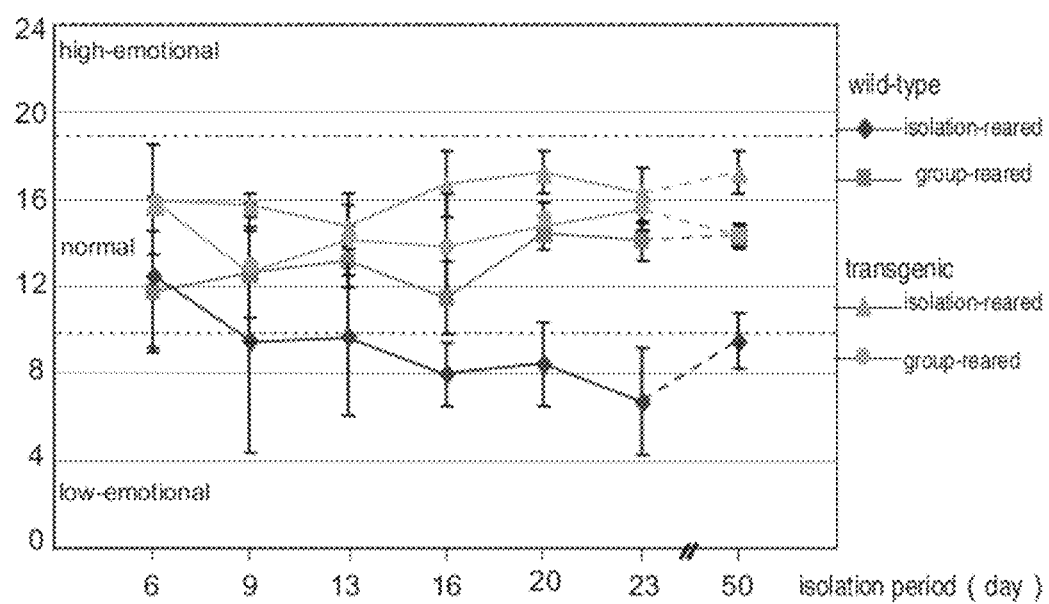

SEQUENCE LISTING

```
<160> NUMBER OF SEQ ID NOS: 4

<210> SEQ ID NO 1
<211> LENGTH: 458
<212> TYPE: PRT
<213> ORGANISM: Homo sapiens

<400> SEQUENCE: 1

Met Gly Leu Cys Tyr Ser Leu Arg Pro Leu Leu Phe Gly Gly Pro Gly
 1               5                   10                  15

Asp Asp Pro Cys Ala Ala Ser Glu Pro Pro Val Glu Asp Ala Gln Pro
                20                  25                  30

Ala Pro Ala Pro Ala Leu Ala Pro Val Arg Ala Ala Ala Arg Asp Thr
            35                  40                  45

Ala Arg Thr Leu Leu Pro Arg Gly Gly Glu Gly Ser Pro Ala Cys Ala
        50                  55                  60

Arg Pro Lys Ala Asp Lys Pro Lys Glu Lys Arg Gln Arg Thr Glu Gln
 65                  70                  75                  80

Leu Ser Ala Glu Glu Arg Glu Ala Ala Lys Glu Arg Glu Ala Val Lys
                85                  90                  95

Glu Ala Arg Lys Val Ser Arg Gly Ile Asp Arg Met Leu Arg Asp Gln
            100                 105                 110

Lys Arg Asp Leu Gln Gln Thr His Arg Leu Leu Leu Leu Gly Ala Gly
        115                 120                 125

Glu Ser Gly Lys Ser Thr Ile Val Lys Gln Met Arg Ile Leu His Val
    130                 135                 140

Asn Gly Phe Asn Pro Glu Glu Lys Lys Gln Lys Ile Leu Asp Ile Arg
145                 150                 155                 160

Lys Asn Val Lys Asp Ala Ile Val Thr Ile Val Ser Ala Met Ser Thr
                165                 170                 175

Ile Ile Pro Pro Val Pro Leu Ala Asn Pro Glu Asn Gln Phe Arg Ser
            180                 185                 190

Asp Tyr Ile Lys Ser Ile Ala Pro Ile Thr Asp Phe Glu Tyr Ser Gln
        195                 200                 205

Glu Phe Phe Asp His Val Lys Lys Leu Trp Asp Asp Glu Gly Val Lys
    210                 215                 220
```

```
Ala Cys Phe Glu Arg Ser Asn Glu Tyr Gln Leu Ile Asp Cys Ala Gln
225                 230                 235                 240

Tyr Phe Leu Glu Arg Ile Asp Ser Val Ser Leu Val Asp Tyr Thr Pro
            245                 250                 255

Thr Asp Gln Asp Leu Leu Arg Cys Arg Val Leu Thr Ser Gly Ile Phe
        260                 265                 270

Glu Thr Arg Phe Gln Val Asp Lys Val Asn Phe His Met Phe Asp Val
    275                 280                 285

Gly Gly Gln Arg Asp Glu Arg Arg Lys Trp Ile Gln Cys Phe Asn Asp
290                 295                 300

Val Thr Ala Ile Ile Tyr Val Ala Ala Cys Ser Ser Tyr Asn Met Val
305                 310                 315                 320

Ile Arg Glu Asp Asn Asn Thr Asn Arg Leu Arg Glu Ser Leu Asp Leu
                325                 330                 335

Phe Glu Ser Ile Trp Asn Asn Arg Trp Leu Arg Thr Ile Ser Ile Ile
            340                 345                 350

Leu Phe Leu Asn Lys Gln Asp Met Leu Ala Glu Lys Val Leu Ala Gly
        355                 360                 365

Lys Ser Lys Ile Glu Asp Tyr Phe Pro Glu Tyr Ala Asn Tyr Thr Val
    370                 375                 380

Pro Glu Asp Ala Thr Pro Asp Ala Gly Glu Asp Pro Lys Val Thr Arg
385                 390                 395                 400

Ala Lys Phe Phe Ile Arg Asp Leu Phe Leu Arg Ile Ser Thr Ala Thr
                405                 410                 415

Gly Asp Gly Lys His Tyr Cys Tyr Pro His Phe Thr Cys Ala Val Asp
            420                 425                 430

Thr Glu Asn Ile Arg Arg Val Phe Asn Asp Cys Arg Asp Ile Ile Gln
        435                 440                 445

Arg Met His Leu Lys Gln Tyr Glu Leu Leu
    450                 455
```

<210> SEQ ID NO 2
<211> LENGTH: 1377
<212> TYPE: DNA
<213> ORGANISM: Homo sapiens
<220> FEATURE:
<221> NAME/KEY: CDS
<222> LOCATION: (1)..(1377)

<400> SEQUENCE: 2

```
atg ggt ctg tgc tac agt ctg cgg ccg ctg ctt ttc ggg ggc cca ggg    48
Met Gly Leu Cys Tyr Ser Leu Arg Pro Leu Leu Phe Gly Gly Pro Gly
  1               5                  10                  15 gac gac ccc tgc gcg gcc tcg gag ccg ccg gtg gag gac gcg cag ccc    96
Asp Asp Pro Cys Ala Ala Ser Glu Pro Pro Val Glu Asp Ala Gln Pro
             20                  25                  30 gcc ccg gcc ccg gcc ctg gcc cca gtc cgg gcg gcc gca agg gac acg   144
Ala Pro Ala Pro Ala Leu Ala Pro Val Arg Ala Ala Ala Arg Asp Thr
         35                  40                  45 gcc cgg acc ctg ctc cct cgg ggc ggc gaa ggg agc ccg gca tgc gct   192
Ala Arg Thr Leu Leu Pro Arg Gly Gly Glu Gly Ser Pro Ala Cys Ala
     50                  55                  60 cgg ccc aaa gca gac aag ccg aag gag aag cgg cag cgc acc gag cag   240
Arg Pro Lys Ala Asp Lys Pro Lys Glu Lys Arg Gln Arg Thr Glu Gln
 65                  70                  75                  80 ctg agt gcc gag gag cgc gag gcg gcc aag gag cgc gag gcg gtc aag   288
Leu Ser Ala Glu Glu Arg Glu Ala Ala Lys Glu Arg Glu Ala Val Lys
                 85                  90                  95
```

| | | | | | | | | | | | | | | | | |
|---|---|---|---|---|---|---|---|---|---|---|---|---|---|---|---|---|
| gag | gcg | agg | aaa | gtg | agc | cgg | ggc | atc | gac | cgc | atg | ctg | cgc | gac | cag | 336 |
| Glu | Ala | Arg | Lys | Val | Ser | Arg | Gly | Ile | Asp | Arg | Met | Leu | Arg | Asp | Gln | |
| | | | 100 | | | | 105 | | | | 110 | | | | | |
| aag | cgc | gac | ctg | cag | cag | acg | cac | cgg | ctc | ctg | ctc | ggg | gct | ggt | | 384 |
| Lys | Arg | Asp | Leu | Gln | Gln | Thr | His | Arg | Leu | Leu | Leu | Gly | Ala | Gly | | |
| | | 115 | | | | | 120 | | | | | 125 | | | | |
| gag | tct | ggg | aaa | agc | acc | atc | gtc | aaa | cag | atg | agg | atc | ctg | cac | gtc | 432 |
| Glu | Ser | Gly | Lys | Ser | Thr | Ile | Val | Lys | Gln | Met | Arg | Ile | Leu | His | Val | |
| | 130 | | | | | 135 | | | | | 140 | | | | | |
| aat | ggg | ttt | aat | ccc | gag | gaa | aag | aaa | cag | aaa | att | ctg | gac | atc | cgg | 480 |
| Asn | Gly | Phe | Asn | Pro | Glu | Glu | Lys | Lys | Gln | Lys | Ile | Leu | Asp | Ile | Arg | |
| 145 | | | | | 150 | | | | | 155 | | | | | 160 | |
| aaa | aat | gtt | aaa | gat | gct | atc | gtg | aca | att | gtt | tca | gca | atg | agt | act | 528 |
| Lys | Asn | Val | Lys | Asp | Ala | Ile | Val | Thr | Ile | Val | Ser | Ala | Met | Ser | Thr | |
| | | | | 165 | | | | | 170 | | | | | 175 | | |
| ata | ata | cct | cca | gtt | ccg | ctg | gcc | aac | cct | gaa | aac | caa | ttt | cga | tca | 576 |
| Ile | Ile | Pro | Pro | Val | Pro | Leu | Ala | Asn | Pro | Glu | Asn | Gln | Phe | Arg | Ser | |
| | | | | 180 | | | | | 185 | | | | | 190 | | |
| gac | tac | atc | aag | agc | ata | gcc | cct | atc | act | gac | ttt | gaa | tat | tcc | cag | 624 |
| Asp | Tyr | Ile | Lys | Ser | Ile | Ala | Pro | Ile | Thr | Asp | Phe | Glu | Tyr | Ser | Gln | |
| | | | 195 | | | | | 200 | | | | | 205 | | | |
| gaa | ttc | ttt | gac | cat | gtg | aaa | aaa | ctt | tgg | gac | gat | gaa | ggc | gtg | aag | 672 |
| Glu | Phe | Phe | Asp | His | Val | Lys | Lys | Leu | Trp | Asp | Asp | Glu | Gly | Val | Lys | |
| | 210 | | | | | 215 | | | | | 220 | | | | | |
| gca | tgc | ttt | gag | aga | tcc | aac | gaa | tac | cag | ctg | att | gac | tgt | gca | caa | 720 |
| Ala | Cys | Phe | Glu | Arg | Ser | Asn | Glu | Tyr | Gln | Leu | Ile | Asp | Cys | Ala | Gln | |
| 225 | | | | | 230 | | | | | 235 | | | | | 240 | |
| tac | ttc | ctg | gaa | aga | atc | gac | agc | gtc | agc | ttg | gtt | gac | tac | aca | ccc | 768 |
| Tyr | Phe | Leu | Glu | Arg | Ile | Asp | Ser | Val | Ser | Leu | Val | Asp | Tyr | Thr | Pro | |
| | | | | 245 | | | | | 250 | | | | | 255 | | |
| aca | gac | cag | gac | ctc | ctc | aga | tgc | aga | gtt | ctg | aca | tct | ggg | att | ttt | 816 |
| Thr | Asp | Gln | Asp | Leu | Leu | Arg | Cys | Arg | Val | Leu | Thr | Ser | Gly | Ile | Phe | |
| | | | 260 | | | | | 265 | | | | | 270 | | | |
| gag | aca | cga | ttc | caa | gtg | gac | aaa | gta | aac | ttc | cac | atg | ttt | gat | gtt | 864 |
| Glu | Thr | Arg | Phe | Gln | Val | Asp | Lys | Val | Asn | Phe | His | Met | Phe | Asp | Val | |
| | | 275 | | | | | 280 | | | | | 285 | | | | |
| ggt | ggc | cag | agg | gat | gag | agg | aga | aaa | tgg | atc | cag | tgc | ttt | aac | gat | 912 |
| Gly | Gly | Gln | Arg | Asp | Glu | Arg | Arg | Lys | Trp | Ile | Gln | Cys | Phe | Asn | Asp | |
| | 290 | | | | | 295 | | | | | 300 | | | | | |
| gtc | aca | gct | atc | att | tac | gtc | gca | gcc | tgc | agt | agc | tac | aac | atg | gtg | 960 |
| Val | Thr | Ala | Ile | Ile | Tyr | Val | Ala | Ala | Cys | Ser | Ser | Tyr | Asn | Met | Val | |
| 305 | | | | 310 | | | | | 315 | | | | | 320 | | |
| att | cga | gaa | gat | aac | aac | acc | aac | agg | ctg | aga | gag | tcc | ctg | gat | ctt | 1008 |
| Ile | Arg | Glu | Asp | Asn | Asn | Thr | Asn | Arg | Leu | Arg | Glu | Ser | Leu | Asp | Leu | |
| | | | | 325 | | | | | 330 | | | | | 335 | | |
| ttt | gaa | agc | atc | tgg | aac | aac | agg | tgg | tta | cgg | acc | att | tct | atc | atc | 1056 |
| Phe | Glu | Ser | Ile | Trp | Asn | Asn | Arg | Trp | Leu | Arg | Thr | Ile | Ser | Ile | Ile | |
| | | | 340 | | | | | 345 | | | | | 350 | | | |
| ttg | ttc | ttg | aac | aaa | caa | gat | atg | ctg | gca | gaa | aaa | gtc | ttg | gca | ggg | 1104 |
| Leu | Phe | Leu | Asn | Lys | Gln | Asp | Met | Leu | Ala | Glu | Lys | Val | Leu | Ala | Gly | |
| | | 355 | | | | | 360 | | | | | 365 | | | | |
| aaa | tca | aaa | att | gaa | gac | tat | ttc | cca | gaa | tat | gca | aat | tat | act | gtt | 1152 |
| Lys | Ser | Lys | Ile | Glu | Asp | Tyr | Phe | Pro | Glu | Tyr | Ala | Asn | Tyr | Thr | Val | |
| | 370 | | | | | 375 | | | | | 380 | | | | | |
| cct | gaa | gac | gca | aca | cca | gat | gca | gga | gaa | gat | ccc | aaa | gtt | aca | aga | 1200 |
| Pro | Glu | Asp | Ala | Thr | Pro | Asp | Ala | Gly | Glu | Asp | Pro | Lys | Val | Thr | Arg | |
| 385 | | | | | 390 | | | | | 395 | | | | | 400 | |
| gcc | aag | ttc | ttt | atc | cgg | gac | ctg | ttt | ttg | agg | atc | agc | acg | gcc | acc | 1248 |
| Ala | Lys | Phe | Phe | Ile | Arg | Asp | Leu | Phe | Leu | Arg | Ile | Ser | Thr | Ala | Thr | |
| | | | | 405 | | | | | 410 | | | | | 415 | | |

```
ggt gac ggc aaa cat tac tgc tac ccg cac ttc acc tgc gcc gtg gac    1296
Gly Asp Gly Lys His Tyr Cys Tyr Pro His Phe Thr Cys Ala Val Asp
            420                 425                 430 aca gag aac atc cgc agg gtg ttc aac gac tgc cgc gac atc atc cag    1344
Thr Glu Asn Ile Arg Arg Val Phe Asn Asp Cys Arg Asp Ile Ile Gln
        435                 440                 445 cgg atg cac ctc aag cag tat gag ctc ttg tga                        1377
Arg Met His Leu Lys Gln Tyr Glu Leu Leu
    450                 455

<210> SEQ ID NO 3
<211> LENGTH: 26
<212> TYPE: DNA
<213> ORGANISM: Artificial sequence
<220> FEATURE:
<223> OTHER INFORMATION: Designed oligonucleotide primer for PCR

<400> SEQUENCE: 3
atgctgcgcg accagaagcg cgacct                                       26

<210> SEQ ID NO 4
<211> LENGTH: 25
<212> TYPE: DNA
<213> ORGANISM: Artificial sequence
<220> FEATURE:
<223> OTHER INFORMATION: Designed oligonucleotide primer for PCR

<400> SEQUENCE: 4
agtcagtgat aggggctatg ctctt                                        25
```

US 8,193,146 B2

METHOD OF AMELIORATING SYMPTOM CAUSED BY MOOD DISTURBANCE

CROSS-REFERENCE TO RELATED APPLICATION

This application is a Section 371 of International Application No. PCT/JP2006/305633, filed Mar. 15, 2006 which was published in the Japanese language on Sep. 21, 2006, under International Publication No. 2006/098488 A1, the disclosure of which is hereby incorporated herein by reference.

TECHNICAL FIELD

The present invention relates to a method for improving symptom of mood disorder or its related disorder and the like.

BACKGROUND ART

Use of a certain compound in preparing a medicament used in treating mood disorder, particularly, depression is known (WO00/61125 gazette).

In addition, a protein (Gm1 protein) is known (US 2005/260595), the protein containing: a domain having high sequence identity with a GTP-binding site and a GTPase activation site which are conserved among G-protein α subunits, and an amino acid sequence having high sequence identity with a trimer-forming domain conserved among G-protein α subunits. The protein is reported to be involved in intracellular signal transduction due to G protein-coupled receptor (GPCR) stimulation, and expressed in human brain, thymus, testis, spleen, small intestine, uterine and heart. And, a method for screening a cellular signal transduction regulating substance using a polynucleotide encoding the protein is disclosed.

DISCLOSURE OF THE INVENTION

An object of the present invention is to provide, for example, a method for improving symptom of "mood disorder or its related disorders" such as depression and anxiety. Another object is to provide a method for searching a substance which is an active ingredient of a medicament useful for treating the "mood disorder or its related disorders", and a model mammal utilized in the method and the like.

That is, the present invention provides:
1. a method for improving symptom of mood disorder or its related disorder comprising a step of allowing any one of the following proteins and polypeptides to be excessively present in a brain of a mammal (hereinafter, referred to as the present improving method in some cases);
    (a) a Gm1 protein,
    (b) a protein comprising an amino acid sequence in which one or a plurality of amino acids are deleted, added or substituted in a Gm1 protein, and having function as a Gm1 protein,
    (c) a polypeptide comprising a part of a Gm1 protein, and having function as a Gm1 protein, and
    (d) a polypeptide comprising an amino acid sequence having 85% or more sequence identity with a Gm1 protein, and having function as a Gm1 protein;
2. a non-human mammal, to which the method as defined in the above 1 has been applied (hereinafter, referred to as the present mammal in some cases) or a part thereof;
3. a transgenic non-human mammal individual or a progeny thereof or a part thereof, in which an expression level of any one of the following genes and polynucleotides is substantially increased than an expression level of the same gene in a wild-type mammal of the same species (hereinafter, referred to as present transgenic mammal in some cases);
    (a) a Gm1 gene,
    (b) a gene comprising a nucleotide sequence in which one or a plurality of nucleotides are deleted, added or substituted in a Gm1 gene, wherein a translation product of the gene has function as a Gm1 protein,
    (c) a polynucleotide comprising a part of a Gm1 gene, wherein a translation product of the polynucleotide has function as a Gm1 protein, and
    (d) a polynucleotide comprising a nucleotide sequence having 85% or more sequence identity with a nucleotide sequence of a Gm1 gene, wherein a translation product of the polynucleotide has function as a Gm1 protein;
4. the transgenic non-human mammal or a part thereof according to the above 3, wherein the transgenic non-human mammal is a mouse;
5. the transgenic non-human mammal or a part thereof according to the above 3 or 4, wherein the transgenic non-human mammal individual or a progeny thereof or a part thereof is a tissue or a cell derived from the transgenic non-human mammal;
6. use of any one of the following proteins and polypeptides for producing a medicament useful for treating mood disorder or its related disorder (hereinafter, referred to as the present protein use in some cases);
    (a) a Gm1 protein,
    (b) a protein comprising an amino acid sequence in which one or a plurality of amino acids are deleted, added or substituted in a Gm1 protein, and having function as a Gm1 protein,
    (c) a polypeptide comprising a part of a Gm1 protein, and having function as a Gm1 protein, and
    (d) a polypeptide comprising an amino acid sequence having 85% or more sequence identity with a Gm1 protein, and having function as a Gm1 protein;
7. any one of the following proteins and polypeptides for using as a medicament in treating mood disorder or its related disorder (hereinafter, referred to as the present protein for use in medicament in some cases);
    (a) a Gm1 protein,
    (b) a protein comprising an amino acid sequence in which one or a plurality of amino acids are deleted, added or substituted in a Gm1 protein, and having function as a Gm1 protein,
    (c) a polypeptide comprising a part of a Gm1 protein, and having function as a Gm1 proteins and
    (d) a polypeptide comprising an amino acid sequence having 85% or more sequence identity with a Gm1 protein, and having function as a Gm1 protein;
8. a pharmaceutical composition for treating mood disorder or its related disorder containing any one of the following proteins and polypeptides, and a pharmaceutically acceptable carrier (hereinafter, referred to as the present protein composition in some cases);
    (a) a Gm1 protein,
    (b) a protein comprising an amino acid sequence in which one or a plurality of amino acids are deleted, added or substituted in a Gm1 protein, and having function as a Gm1 protein,
    (a) a polypeptide comprising a part of a Gm1 protein, and having function as a Gm1 protein, and
    (d) a polypeptide comprising an amino acid sequence having 85% or more sequence identity with a Gm1 protein, and having function as a Gm1 protein;

9. use of any one of the following genes and polynucleotides for preparing a medicament useful for treating mood disorder or its related disorder (hereinafter, collectively, referred to as the present gene use in some cases);
   (a) a Gm1 gene.
   (b) a gene comprising a nucleotide sequence in which one or a plurality of nucleotides are deleted, added or substituted in a Gm1 gene, wherein a translation product of the gene has function as a Gm1 protein,
   (c) a polynucleotide comprising a part of a Gm1 gene, wherein a translation product of the polynucleotide has function as a Gm1 protein,
   (d) a polynucleotide comprising a nucleotide sequence having 85% or more sequence identity with a nucleotide sequence of a Gm1 gene, wherein a translation product of the polynucleotide has function as a Gm1 protein, and
   (e) a vector containing any one of genes and polynucleotides of (a) to (d);
10. any one of the following genes and polynucleotides for use as a medicament in treating mood disorder or its related disorder (hereinafter, referred to as the present gene for use as medicament in some cases);
   (a) a Gm1 gene,
   (b) a gene comprising a nucleotide sequence in which one or a plurality of nucleotides are deleted, added or substituted in a Gm1 gene, wherein a translation product of the gene has function as a Gm1 protein,
   (c) a polynucleotide comprising a part of a Gm1 gene, wherein a translation product of the polynucleotide has function as a Gm1 protein,
   (d) a polynucleotide comprising a nucleotide sequence having 85% or more sequence identity with a nucleotide sequence of a Gm1 gene, wherein a translation product of the polynucleotide has function as a Gm1 protein, and
   (e) a vector containing any one of genes and polynucleotides of (a) to (d);
11. a pharmaceutical composition for treating disorder or its related disorder containing any one of the following genes and polynucleotides, and a pharmaceutically acceptable carrier (hereinafter, referred to as the present gene composition in some cases);
   (a) a Gm1 gene,
   (b) a gene comprising a nucleotide sequence in which one or a plurality of nucleotides are deleted, added or substituted in a Gm1 gene, wherein a translation product of the gene has function as a Gm1 protein,
   (c) a polynucleotide comprising a part of a Gm1 gene, wherein a translation product of the polynucleotide has function as a Gm1 protein,
   (d) a polynucleotide comprising a nucleotide sequence having 85% or more sequence identity with a nucleotide sequence of a Gm1 gene, wherein a translation product of the polynucleotide has function as a Gm1 protein, and
   (e) a vector containing any one of genes and polynucleotides of (a) to (d);
12. a method for searching a substance which is an active ingredient of a medicament useful for treating mood disorder or its related disorder, comprising:
   (1) a first step of administering a test substance to or contacting a test substance with a mammal or a part thereof;
   (2) a second step of measuring symptom of mood disorder or its related disorder or an index correlated therewith in the mammal or a part thereof to which the test substance is administered, or with which the test substance is contacted;
   (3) a third step of comparing the measured symptom or index with controls, wherein at least one of the controls is symptom of mood disorder or its related disorders or an index correlated therewith, in the mammal or a part thereof as defined in any one of the above 2 to 5; and
   (4) a fourth step of selecting a test substance having an effect of improving symptom of mood disorder or its related disorder, based on a difference obtained by the comparison (hereinafter, referred to as the present searching method 1 in some cases);
13. the method according to the above 12, wherein comparison is further performed with, as a controls symptom of mood disorder or its related disorder or an index correlated therewith, in a mammal or a part thereof of the same species as that of the mammal, to which a test substance is not administered, or with which a test substance is not contacted;
14. the method according to the above 12, wherein comparison is further performed with, as a control, symptom of mood disorder or its related disorder or an index correlated therewith, in a mammal or a part thereof of the same species as that of the mammal, to which a test substance is administered, or with which a test substance is contacted;
15. a method for searching a substance which is an active ingredient of a medicament useful for treating mood disorder or its related disorder, comprising:
   (1) a first step of administering a test substance to or contacting a test substance with a mammal or a part thereof;
   (2) a second step of measuring an expression level of any one of the following genes and polynucleotides in the mammal or a part thereof to which the test substance is administered, or with which the test substance is contacted;
   (3) a third step of comparing the measured level with a control; and
   (4) a fourth step of selecting a test substance having an effect of improving symptom of mood disorder or its related disorder, based on a difference obtained by the comparison (hereinafter, referred to as the present searching method 2 in some cases);
   (a) a Gm1 gene,
   (b) a gene comprising a nucleotide sequence in which one or a plurality of nucleotides are deleted, added or substituted in a Gm1 gene, wherein a translation product of the gene has function as a Gm1 protein,
   (c) a polynucleotide comprising a part of a Gm1 gene, wherein a translation product of the polynucleotide has function as a Gm1 protein, and
   (d) a polynucleotide comprising a nucleotide sequence having 85% or more sequence identity with a nucleotide sequence of a Gm1 gene, wherein a translation product of the polynucleotide has function as a Gm1 protein;
16. the method according to the above 15, wherein the control is an expression level of any one of the above genes and polynucleotides, in a mammal or a part thereof of the same species as that of the mammal, to which a test substance is not administered, or with which a test substance is not contacted;
17. the method according to the above 15, wherein the control is an expression level of any one of the above genes and polynucleotides, in a mammal or a part thereof of the same species as that of the mammal, to which a test substance is administered, or with which a test substance is contacted:
18. the method according to the above 15, wherein the control is an expression level of any one of the above genes and polynucleotides, in a mammal or a part thereof as defined in any one of above 2 to 5 to which a test substance is not administered, or with which a test substance is not contacted;
19. a medicament useful for treating mood disorder or its related disorder, comprising as an active ingredient a substance which is selected by the searching method as defined in any one of the above 12 to 18:

20. a method for improving symptom of mood disorder or its related disorder, comprising a step of selecting a test substance having an effect of improving symptom of mood disorder or its related disorder by the searching method as defined in any one of above 12 to 18, and a step of administering the selected substance to a mammal patient in need of a treatment of improving symptom of mood disorder or its related disorder;

21. a method for determining susceptibility of an individual of a mammal for mood disorder or its related disorder, comprising:
(1) a step of obtaining a protein sample from the Individual, and
(2) a step of measuring abundance of any one of the following proteins and polypeptides in the protein sample (hereinafter, referred to as the present determination method 1 in some cases):
(a) a Gm1 protein,
(b) a protein comprising an amino acid sequence in which one or a plurality of amino acids are deleted, added or substituted in a 5 ml protein, and having function as a Gm1 protein,
(c) a polypeptide comprising a part of a Gm1 protein, and having function as a Gm1 protein, and
(d) a polypeptide comprising an amino acid sequence having 85% or more sequence identity with a Gm1 protein, and having function as a Gm1 protein;

22. a method for determining susceptibility of an individual of a mammal for mood disorder or its related disorder, comprising:
(1) a step of obtaining a nucleic acid sample from the individual, and
(2) a step of measuring a transcription level of any one of the following genes and polynucleotides in the nucleic acid sample, or a step of assaying a type of polymorphism of any one of the following genes and polynucleotides in the nucleic acid sample (hereinafter, referred to as the present determination method 2 in some cases);
(a) a Gm1 gene,
(b) a gene comprising a nucleotide sequence in which one or a plurality of nucleotides are deleted, added or substituted in a Gm1 gene, wherein a translation product of the gene has function as a Gm1 protein.
(c) a polynucleotide comprising a part of a Gm1 gene, wherein a translation product of the polynucleotide has function as a Gm1 protein, and
(d) a polynucleotide comprising a nucleotide sequence having 85% or more sequence identity with a nucleotide sequence of a Gm1 gene, wherein a translation product of the polynucleotide has function as a Gm1 protein; and the like.

BRIEF DESCRIPTION OF THE DRAWINGS

FIG. 1 is a view showing the results of an isolation rearing test in a Gm1 transgenic mouse in which a Gm1 protein has been excessively expressed in a brain.

BEST MODE FOR CARRYING OUT THE INVENTION

In the present invention, a molecular biological procedure such as preparation of a DNA and preparation of a vector, a protein chemical procedure such as extraction of a protein and Western blotting, and a procedure such as preparation of a knockout non-human mammal can be performed by methods or methods according to them described in experimental documents such as Molecular Cloning, A Laboratory Manual (T. Maniatis et al., Cold Spring Harbor Laboratory (1982)), New Biochemistry Experimental Course (edited by The Japanese Biochemical Society: Tokyo Kagaku Dojin Co. Ltd.), Gene Targeting (Shinichi Aizawa; Yodosha Co., Ltd. (1995)) and the like.

The "mood disorder and its related disorder" in the present invention means a disorder such as mood disorder (DSM-IV Code; 296. XX, 300.4, 311, 301.13, 295.70), schizophrenia and its related disorder (DSM-IV Code: 295. XX, 297.1, 298.8, 297.3. 298.9), anxiety disorder (DSM-IV Code; 300. XX, 309.81, 308.3), adaptation disorder (DSM-IV Code: 309. XX), personality abnormality (DSM-IV Code: 301. XX), and the like.

In addition, the "Gm1 protein" in the present invention is the known protein described, for example, in US 2005/260595 gazette (i.e. "Gm1 protein" in the same publication gazette), and is a protein called "α subunit Gm1 of trimeric G-protein". Specifically, examples include a Gm1 protein derived from a human comprising the amino acid sequence of SEQ ID NO: 1 (the sequence is also shown in SEQ ID NO: 1 in the present application), which is described in the publication gazette. A nucleotide sequence encoding an amino acid sequence of the protein is the nucleotide sequence of SEQ ID NO: 2 described in the same publication gazette (the sequence is also shown in SEQ ID NO: 2 in the present application), and the like. Further, there can be exemplified a Gm1 protein derived from a mouse comprising an amino acid sequence of SEQ ID NO: 25 described in the same publication gazette, and a Gm1 protein derived from a rat comprising an amino acid sequence of SEQ ID NO: 26, which is described in the same publication gazette.

Such the α subunit Gm1 of trimeric G-protein is involved in pathogenesis of a disease due to the "mood disorder or its related disorder" such as depression and anxiety. In neurons of a patient with depression or anxiety, expression of the protein was depressed. When the protein was excessively expressed in a brain of a model mammal, resistance against various stresses was exhibited in a mammal with forced expression of Gm1 in its brain.

The present improving method comprises a step of allowing any one of the following proteins and polypeptides (hereinafter, collectively, referred to as the present protein in some cases) to be excessively present in a brain of a mammal:
(a) a Gm1 protein,
(b) a protein comprising an amino acid sequence in which one or a plurality of amino acids are deleted, added or substituted in a Gm1 protein, and having function as a Gm1 protein,
(c) a polypeptide comprising a part of a Gm1 protein, and having function as a Gm1 protein, and
(d) a polypeptide comprising an amino acid sequence having 85% or more sequence identity with a Gm1 protein, and having function as a Gm1 protein.

Herein, the "present protein" may be a part of the protein as far as it does not damage the function of a Gm1 protein, as described above. An amino acid sequence of SEQ ID NO: 1 has an amino acid sequence having high amino acid sequence identity with amino acid sequences at a GTP binding site and a GTPase activation site conserved between G protein α subunits. These sequences are respective sequences represented by amino acid numbers 126 to 133, 287 to 292, 353 to 359, and 428 to 435 in an amino acid sequence of SEQ ID NO: 1. These amino acid sequences are consisting of amino acid sequences of a GTP binding site and a GTPase activation site of Gs and Golf which have been already identified as a G protein α subunit (NATURE, 117-127, 1991, vol. 349). In addition, the amino acid sequence of SEQ ID NO: 1 has the same sequence as a characteristic sequence conserved between G protein α subunits, particularly between Gs and Golf belonging to a Gs family (amino acid numbers 119 to 126 of SEQ ID NO: 1) and, moreover, can take an α helix structure conserved between G protein α subunits.

The present protein includes, for example, in addition to the protein, a salt or a derivative thereof to such an extent that the biological function is not damaged. Examples of such the derivative include a derivative in which a C-terminal or other carboxyl group is converted into amide, ester or the like, a derivative in which a N-terminal or other amino group is protected with a formyl group, an acyl group or the like, etc And, as the salt, an acid addition salt is preferable. Examples of the acid addition salt include salts with inorganic acids such as hydrochloric acid, phosphoric acid, sulfuric acid and the like; salts with organic acids such as formic acid, acetic acid, propionic acid and the like.

Further, an index of what and how many amino acid residues can be substituted, deleted or added without losing the biological function can be found out by the method described in US 2005/260595 gazette, etc. Alteration without losing the biological function can be performed, for example, on a part having low sequence identity with amino acid sequences of the already identified various G protein α subunits.

Herein, the "an amino acid sequence in which amino acids are deleted, added or substituted" described in the (b), "a part of a protein" described in the (c), and the "an amino acid sequence having 85% or more sequence identity" described in the (d) include naturally occurring mutations due to processing which a protein comprising the amino acid sequence of SEQ ID NO: 1 undergoes in a cell, a spices difference or an individual difference between organisms from which the protein is derived, a difference between tissues from which the protein is derived or the like, artificial amino acid mutations, and the like.

An example of an artificial procedure for the "deletion, addition or substitution of amino acid" described in the (b) (hereinafter, collectively referred to as "alteration of amino acid") comprises introducing a mutation into a DNA encoding the amino acid sequence of SEQ ID NO: 1 by a conventional site-specific mutagenesis method and then expressing said DNA by a conventional method. Herein, examples of the site-specific mutagenesis method include a method utilizing amber mutation (gapped duplex method, Nucleic Acids Res., 12, 9441-9456 (1986)), a PCR method using primers for introducing a mutation, and the like.

The number of amino acids to be altered as described above is at least one residue, specifically 1 or a few, or more. The number of such alteration may be in such a range that an activity for ameliorating allergy disease symptoms can be found in the present protein.

Among the aforementioned deletion, addition and substitution, alteration involving substitution of amino acid is particularly preferred. More preferably, the substitution is substitution with amino acid whose properties such as hydrophobicity, charge, pK, a steric structural characteristic and the like are similar. Examples of such substitution include substitution within the groups of i) glycine, alanine (nonpolar amino acid); ii) valine, isoleucine, leucine (nonpolar amino acid); iii) aspartic acid, glutamic acid (acidic amino acid), asparagine, glutamine (polar amino acid); iv) serine, threonine (polar amino acid); v) lysine, arginine, histidine (basic amino acid); vi) phenylalanine, tyrosine, tryptophan (amino acid with aromatic side chain).

The "sequence identity" in the present invention refers to identity and homology between two DNA or two proteins. The "sequence identity" is determined by comparing two sequences aligned in the optimal state, over the region of a sequence to be compared. Herein, a nucleic acid or protein to be compared may have addition or deletion (e.g. gap etc.) in the optimal alignment of two sequences. Such sequence identity can be calculated by producing alignment utilizing the ClustalW algorism (Nucleic Acid Res., 22(22):4673-4680 (1994)), for example, using Vector NTI. The sequence identity is determined using sequence analysis software, specifically, Vector NTI or GENETYX-MAC, or an analysis tool provided in public database. The public database is generally available, for example, in a website of DNA Data Bank of Japan [an international DNA data bank operated in Center for International Biology and DNA Data Bank of Japan; CIB/DDBJ)] or the like.

The sequence identity in the present invention is 85% or more, preferably 90% or mores more preferably 95% or more at the amino acid level. At the nucleic acid level, the sequence identity is 85% or more, preferably 90% or more, more preferably 95% or more.

Regarding the a polypeptide comprising an amino acid sequence having 85% or more sequence identity with a Gm1 protein of the (d), a DNA comprising a nucleotide sequence encoding it can be obtained, for example, by using, as an indicator, hybridization with a DNA comprising a nucleotide sequence complementary to a nucleotide sequence encoding an amino acid sequence of Gm1 protein under a stringent condition. The hybridization used herein can be performed according to a conventional method described in, for examples Sambrook J., Frisch E F., Maniatis, T., Molecular Cloning 2$^{nd}$ edition, Cold Spring Harbor Laboratory Press or the like. An example of the "stringent conditions" is hybridization at 45° C. in a solution containing 6×SSC (a solution containing 1.5 M NaCl and 0.15 M trisodium citrate is defined as 10×SSC) and 50% formamide, followed by washing with 2×SSC at 50° C. (Molecular Biology, John Wiley & Sons, N.Y. (1989), 6.3.1-6.3.6). The salt concentration in a washing step can be selected, for example, from the range of 2×SSC at 50° C. (low stringent condition) to 0.2×SSC at 50° C. (high stringent condition). The temperature in a washing step can be selected, for example, from the range of room temperature (low stringent condition) to 65° C. (high stringent condition). In addition, both the salt concentration and the temperature may be changed.

The "having function as a Gm1 protein" means that the function of amplifying and transducing a signal given by a receptor by binding of a physiologically active substance such as a hormone, an autacoid, a neurotransmitter and the like in a living body is possessed, specifically, that a role as a transmitter carrying a signal of stimulation undergone by a G protein-coupled receptor (hereinafter, referred to as "GPCR"; G protein coupled receptor) which is a seven time transmembrane receptor into a cell is played. It has been revealed that GPCR is expressed in wide kinds of tissues and its signal transduction system mediates in expression of a wide cell functions such as hormone reception, neurotransmission, and cell proliferation and differentiation (for example, see Modern Chemistry Extra Edition 34, 61-70, 1997 etc.). To describe in detail, for example, when a ligand such as a hormone and a neurotransmitter is bound to GPCR present on a membrane surface, GPCR is activated, and the signal is transmitted to G-protein. In the G-protein to which a signal has been transmitted, GDP is released from an inactivated type α subunit to which GDP is bound, and the α subunit is converted into an activated type to which GDP is bound in place of the GDP. The present protein has function that is involved in intracellular signal transduction due to stimulation of a G protein-coupled receptor as an α subunit of G-protein.

As the "mammal", any mammal can be used, and examples of an experimental animal include a non-human mammal Examples of such the mammal include a cow, pig, sheep, gout, monkey, dog, cat, rabbit, guinea pig, hamster, mouse, rat, horse, cat and the like. Among them, a rodent mammal which is relatively short in a term necessary for individual generation and an organism cycle, and is easily reared, particularly a mouse is preferable. Representative examples of the mouse used include C57BL/6 line, BALB/c line, DBA2 line and the like as a pure line, and B6C3F1 line, BDF1 line, B6D2F1 line, ICR line and the like as a cross line and, inter alia, C57BL/6 strain is preferably used.

In order to allow the present protein "to be excessively present in a brain of a mammal", for example, a method of controlling abundance of the present protein such as a Gm1 protein and the like in a brain by controlling an expression level of the present gene such as a Gm1 gene and the like in a brain (specifically, examples include a method of introducing DNA in which the present gene is linked to the downstream of a suitable promoter inducing expression in a brain, into one or more places on a chromosome of the mammal, a method of introducing the present gene using a virus vector and the like), a method of controlling abundance of the present protein such as a Gm1 protein and the like in a brain without controlling an expression level of the present gene such as a Gm1 gene and the like in a brain (specifically, a method of microinjecting the present protein directly into a brain) and the like may be used.

As used herein, "excessively" refers to the state where abundance of the present protein in a brain is substantially higher as compared with abundance in a brain in a wild-type mammal Examples include the state where a treatment of increasing abundance of the present protein in a brain was performed in a subject mammal.

The present mammal is characterized in that the animal is subjected to the present improving method. In the mammal, the present protein such as a Gm1 protein and the like is excessively present in a brain. A non-human mammal in which expression level of the present gene is substantially increased by subjecting the non-human mammal to a procedure of introducing the present gene or a procedure of mutating other gene (e.g. present transgenic mammal) is included in the present mammal. And, the present mammal can be also utilized as an index of a drug efficacy when the effect of a test substance as a drug for treating mood disorder or its related disorder is assessed.

Examples of the "part" of the present mammal include a tissue and a cell derived from the mammal, preferably a brain tissue and the like. In addition, a body liquid such as blood, lymph liquid and urine derived from the mammal is also included in the part of the present mammal.

Further, not only a cultured cell obtained by isolating and culturing a cell contained in the tissue, internal organ or body liquid (including a taken first generation primary cell and a cell obtained by establishing the primary cell) and an extract, but also each organ at a developmental stage at an embryonal embryo, and an accompanying cell culture and an ES cell are included in the "part" of a non-human animal regardless of the presence or the absence of the differentiating and proliferating ability.

A method of producing a mammal in which expression of a protein encoded by a particular gene is increased, by introducing the gene, is known as such, and any of the known methods may be used for introducing the present gene such as a Gm1 gene and the like into a mammal. Specifically, for example, a DNA in which the present gene is ligated downstream of a promoter which can induce expression in a brain, and a polyA addition signal is further ligated downstream therefrom is introduced into a fertilized ovum by microinjection with a micromanipulator. Examples of the promoter which can induce expression in a brain include a brain-specific enolase (hereinafter, referred to as NSE in some cases) gene promoter and a calmodulin kinase II gene promoter. By transplanting the fertilized ovum into a uterine tube of a non-human mammal in the pseudopregnant state (hereinafter, referred to as foster in some cases), a non-human mammal having a transgene is obtained.

It can be known by screening the presence of a transgene by a conventional genetic engineering method or the like that an offspring of a foster is the aforementioned transgenic mammal. For example, a genomic DNA is extracted from a body tissue (e.g. a part of a tail etc.) of the offspring which was born and weaned from the foster. Whether the genomic DNA contains a DNA of an introduced present gene or not is examined. In this procedure, for example, by conducting PCR using a primer complementary with at least a part of the transgene and employing the genomic DNA as a template, whether a DNA fragment derived from an introduced DNA or not is examined. A mammal for which the presence of a DNA of the introduced present gene in the genomic DNA has been confirmed, may be identified as a transgenic mammal.

A transgenic non-human mammal is reared and passaged while stable maintenance of the DNA of the introduced present gene is confirmed. Analysis of expression of the present gene in the resulting transgenic non-human mammal can be performed, for example, by a RT-PCR method or the like. For example, regarding an RNA extracted from each tissue of the transgenic non-human mammal, a distribution and a level of expression of the introduced gene is examined by a RT-PCR method. Specifically, for example, an RNA is prepared from a brain tissue of the made transgenic non-human mammal, a reverse transcription reaction is performed using an appropriate primer hybridizing with the present gene employing the prepared RNA as a template and, subsequently, a PCR reaction is performed. After the resulting PCR product is electrophoresed with an agarose gel, the gel is staining with ethidium bromide. Then, by measuring a band intensity while the gel is irradiated with UV, the presence or the absence of the desired DNA fragment may be detected. Preparation of an RNA, an electrophoresis method, a reverse transcription reaction, a PCR reaction, a method of detecting a band intensity and the like may be performed according to the known per se method which is conventionally used.

An analysis of expression of the present protein in the resulting transgenic non-human mammal can be performed, for example, by a Western blotting method or the like. Specifically, for example, a protein extract is prepared from a brain tissue of the made transgenic non-human mammal, and the prepared protein extract is electrophoresed and, thereafter, the is separated present protein is transferred onto an appropriate membrane. Then, the present protein transferred onto the membrane is detected with an anti-present protein antibody (for example, see US 2005/260595 gazette) or the like. Preparation of a protein extract, an electrophoresis method, transfer onto a membrane, a method of detecting the present protein and the like can be performed according to the known per se method which is conventionally used.

As specifically described in Examples below, the above-obtained present mammal exhibits resistance against the mental disorder-like model state induced by addition of a stress. Therefore, excessive presence of the present protein such as a Gm1 protein and the like in a brain is effective in improving disease symptom due to mental disorder resulting from various stresses, and the present protein such as a Gm1 protein and the like or the present gene such as a Gm1 gene and the like has the effect as an active ingredient of a medicament useful in treating mood disorder or its related disorder.

In the present mammal, also a next generation individual obtained by its mating can be passaged and maintained by rearing and passaging it in the conventional rearing environment while substantial increase in an expression amount of the present gene is confirmed. That is, by mating a female or a male of a transgenic non-human mammal in which the present gene has been introduced with a male or a female of a wild-type mammal, a transgenic non-human mammal in which the present gene has been introduced can be passaged. The thus obtained progeny is also included in the present mammal.

By analyzing behavior of the above-obtained present mammal, the function of the present protein such as a Gm1 protein and the like in a living body can be analyzed. As a method of behavioral analysis, any method can be used as far as it can be applied to the mammal and, for example, the method can be performed according to the method described in CURRENT PROTOCOLS IN NEUROSCIENCE (John Wiley & Sons, Inc.), Honyu-Doubutsu-no-Koudou-Kinou-tesuto (Seitai-no-Kagaku, published by Igaku Shoin Ltd., vol. 45, No. 5 (1995)) or the like. Specifically, examples include an open-field test, a balance test walking on bar, a muscle test hanging from wire, a light and dark selection test, an isolation rearing test, a fear conditioning test, a defeat experience test, an electric shock sensitivity test, Morris water maze test, a forced swimming test and the like. Among them, in the present mammal, an isolation rearing test, a fear conditioning test, a defeat experience test, a forced swimming test and the like are preferably used. It is preferable to perform behavioral analysis by combining some methods.

In such the behavioral analysis method, its condition is set so that a change in emotionality or behavior due to an acute or chronic stress can be detected. Therefore, the present mammal and a wild-type mammal (control) are subjected to the behavioral analysis, and respective results are compared. When a significant difference is obtained between the present mammal and the wild-type mammal (control) in a particular test, it can be assessed and determined that the present mammal has any change or effect in symptom which can be behaviorally-analyzed by the test. For example, the present mammal exhibits a significant difference from the wild-type mammals in an isolation rearing test. The isolation rearing test is a method of testing emotionality of a mammal, and is a test which can detect a significant difference in a mammal having symptom of mood disorder or its related disorder (particularly, depression or anxiety). Therefore, it can be assessed and determined that the mammal has resistance to symptom of a disease due to mood disorder or its related disorder (particularly, depression or anxiety). That is, it is seen that excessive presence of the present protein in a brain is useful in improvement (including alleviation, prevention etc.) of symptom of a disease due to mood disorder or its related disorder.

It is preferable that a wild-type mammal which is used as a control in such the behavioral analysis is a litter of the present mammal.

The present protein use is use of the present protein for preparing a medicament useful in treating mood disorder or its related disorder. In addition, the present protein for medicament is the present protein for using as a medicament in treating mood disorder or its related disorder. Further, the present protein composition is a pharmaceutical composition for treating mood disorder or its related disorder, containing the present protein and a pharmaceutically acceptable carrier.

The present protein may be used as a medicament in the following form.

The present protein can be prepared as a pharmaceutical composition for treating mood disorder or its related disorder, as it is, or by mixing with a pharmaceutically acceptable carrier (including excipient, bulking agent, binder, lubricant etc.) and a conventional additive. The pharmaceutical composition can be administered orally or parenterally depending on the prepared form (oral agents such as tablets, pills, capsules, powders, granules, syrups etc.; parenteral agents such as injectables, drips, external agents, suppositories etc.). A dose is different depending on a kind of an active ingredient, an administration route, and an administration subject, and an age, a weight, and condition of a patient, can not be defined unconditionally and, as a daily dose, about 0.01 to 100 mg can be administered once or by dividing into a few times per day.

When the present protein is used as a medicament, it is preferable to use, as an active ingredient of a pharmaceutical composition, a protein which is lowest in antigenicity to a human among the present proteins, and has an amino acid sequence of the present protein or at least a part of it. The present protein can be prepared as a natural protein by a procedure such as extraction, purification and the like from a naturally occurring organism, or can be prepared as a recombinant protein using a genetic engineering procedure. For example, a crude extract is prepared from a cell or a tissue of a human, and a purified protein can be prepared by using a variety of columns. A cell herein is not particularly limited as far as it is producing or expressing the present protein and, for example, a leukocyte-derived cell or the like can be used.

The present gene use is use of any of the following genes and polynucleotides (i.e. present gene) for preparing a medicament useful in treating mood disorder or its related disorder;

(a) a Gm1 gene, (b) a gene comprising a nucleotide sequence in which one or a plurality of nucleotides are deleted, added or substituted in a Gm1 gene, wherein a translation product of the gene has function as a Gm1 protein, (c) a polynucleotide comprising a part of a Gm1 gene, wherein a translation product of the polynucleotide has function as a Gm1 protein, (d) a polynucleotide comprising a nucleotide sequence having 85% or more sequence identity with a nucleotide sequence of a Gm1 gene, wherein a translation product of the polynucleotide has function as a Gm1 protein, and (e) a vector containing any one of genes and polynucleotides of (a) to (d).

Herein, the "present gene" is a polynucleotide comprising a nucleotide sequence encoding an amino acid sequence of the present protein, and other detailed matters may be understood according to the contents explained in the description related to the present protein.

The present gene use is use of the present gene for preparing a medicament useful in treating mood disorder or its related disorder. In addition, the present gene for medicament is the present gene for using as a medicament in treating mood disorder or its related disorder. Further, the present gene composition is a pharmaceutical composition for treating mood disorder or its related disorder, containing the present gene and a pharmaceutically acceptable carrier.

The present gene may be used as a medicament in the following form.

The present gene can be prepared as a pharmaceutical composition for treating mood disorder or its related disorder, as it is, or by mixing with a pharmaceutically acceptable carrier (including excipient, bulking agent, binder, lubricant etc.) and a conventional additive. The pharmaceutical composition can be administered orally or parenterally depending on the prepared form (oral agents such as tablets, pills, capsules, powders, granules, syrups etc.; parenteral agents such as injectables, drips, external agents, suppositories etc.). A dose is different depending on a kind of an active ingredient, an administration route, and an administration subject, and an age, a weight, and condition of a patient, cannot be defined unconditionally and, as a daily dose, about 0.01 to 100 mg can be administered once or by dividing into a few times per day. In addition, the present gene may be introduced into a cell utilizing, for example, a liposome delivery system for encapsulating the present gene into a liposome for delivery, microinjection, a direct injection method, a gene gun or the like. In these cases, a dose and an administration method are different depending on an age, a weight, symptom and the like of a patient, and cannot be defined unconditionally, and a person skilled in the art can appropriately select them. Further, the present gene may be introduced into an objective cell in a form where it is incorporated into a virus vector for gene therapy.

Further, based on a nucleotide sequence possessed by the present gene, an antisense medicament may be developed.

That is, a part or a derivative of the present gene is synthesized by the known method, they can be used to adjust expression of the present protein, or an oligonucleotide comprising a sequence complementary with the present gene, or a derivative thereof can be used to regulate expression of the present protein.

The present searching method 1 is a method for searching a substance which is an active ingredient of a medicament useful in treating mood disorder or its related disorder, comprising (1) a first step of administering a test substance to or contacting a test substance with a mammal or a part thereof; (2) a second step of measuring symptom of mood disorder or its related disorder or an index correlated therewith in the mammal or a part thereof to which the test substance is administered, or with which the test substance is contacted; (3) a third step of comparing the measured symptom or index with controls, wherein at least one of the controls is symptom of mood disorder or its related disorder, or an index correlated therewith, in the present mammal or a part thereof; and (4) a fourth step of selecting a test substance having an effect of improving symptom of mood disorder or its related disorder, based on a difference obtained by the comparison. In the present searching method 1, comparison may be performed, as a control, symptom of mood disorder or its related disorder or an index correlated therewith, in a mammal or a part thereof of the same species as that of the mammal, to which a test substance is not administered, or with which a test substance is not contacted.

The present searching method 2 is a method for searching a substance which is an active ingredient of a medicament useful in treating mood disorder to its related disorder, comprising (1) a first step of administering a test substance to or contacting a test substance with a mammal or a part thereof; (2) a second step of measuring an expression level of any one of the following genes and polynucleotides in the mammal or a part thereof to which the test substance is administered, or with which the test substance is contacted; (3) a third step of comparing the measured level with a control; and (4) a fourth step of selecting a test substance having an effect of improving symptom of mood disorder or its related disorder, based on a difference obtained by the comparison (hereinafter, the present searching method 1 and present searching method 2 are collectively referred to as the present searching methods in some cases):

(a) a Gm1 gene, (b) a gene comprising a nucleotide sequence in which one or a plurality of nucleotides are deleted, added or substituted in a Gm1 gene, wherein a translation product of the gene has function as a Gm1 protein, (c) a polynucleotide comprising a part of a Gm1 gene, wherein a translation product of the polynucleotide has function as a Gm1 protein, and (d) a polynucleotide comprising a nucleotide sequence having 85% or more sequence identity with a nucleotide sequence of a Gm1 gene, wherein a translation product of the polynucleotide has function as a Gm1 protein.

In the present searching method 2, it is preferable that the control is an expression level of any one of the above genes and polynucleotides, in a mammal or a part thereof of the same species as that of the mammal, to which a test substance is not administered, or with which a test substance is not contacted. In addition, examples include one aspect in which the control is an expression level of any one of the above genes and polynucleotides, in a mammal or a part thereof of the same species as that of the mammal, to which a test substance is administered, or with which a test substance is contacted, and one aspect in which the control is an expression level of any one of the above genes and polynucleotides, in the present mammal or a part thereof to which a test substance is not administered, or with which a test substance is not contacted.

In the present invention, the "test substance" is not particularly limited, and is a nucleic acid, a peptide a protein (including an antibody to the present protein), an organic compound, an inorganic compound or the like, and examples include a cell extract, an expression product of a gene library, a synthetic low-molecular organic compound, a synthetic peptide, a synthetic nucleic acid, a natural compound and the like. Herein, examples of the "antibody to the present protein" include an antibody which is immunologically specific for a protein consisting of the amino acid sequence of SEQ ID NO; 1 or its partial region.

By performing the first step and the second step of the present searching method using a positive control or a negative control which can be a "control substance" as the test substance, it can be also a control" referred in the present searching method, depending on the case.

Herein, the "positive control" represents an arbitrary substance having the effect of improving symptom of a disease due to mood disorder or its related disorder. Examples of the "negative control" include a solvent contained in a test substance, a test system solution which is to be a background, and the like.

When the "control substance" is a negative control, if symptom of a disease due to mood disorder or its related disorder, or an index value correlating therewith in the case of administration or contact of a test substance has been improved over symptom of a disease due to mood disorder or its related disorder, or an index value correlating therewith in the case of administration or contact of a control substance, it may be assessed that the test substance has the effect of improving symptom of a disease due to mood disorder or its related disorder. On the other hand, if symptom of a disease due to mood disorder or its related disorder, or an index value correlating therewith in the case of administration or contact of a test substance is equal to or worse than symptom of a disease due to mood disorder or its related disorder, or an index value correlating therewith in the case of administration or contact with a control substance, it may be assessed that the test substance has not the effect of improving symptom of a disease due to mood disorder or its related disorder.

In addition, when the control substance is a positive control, by comparing symptom of a disease due to mood disorder or its related disorder, or an index value correlating therewith in the case of administration or contact of a test substance with symptom of a disease due to mood disorder or its related disorder, or an index value correlating therewith in the case of administration or contact of the control substance, the effect of improving symptom of a disease due to mood disorder or its related disorder of the test substance may be assessed.

The present mammal or a part thereof can be utilized as the animal to which the "positive control" is administered, or with which the "positive control" is contacted, as a part thereof.

Further, the "control" may be symptom of a disease due to mood disorder to its related disorder, or an index value correlating therewith, in the same kind of a mammal to which a test substance is not administered, or with which a test substance is not contacted, as that of the above mammal, or a part thereof.

The "administering a test substance to a mammal, or contacting a test substance with a mammal" in the first step of the present searching method represents administration of the test substance to the mammal, or contact of the test substance with a part of the mammal, and can be performed by the method which is generally used by a person skilled in the art. When the test substance is administered to the mammal, its administration method is not particularly limited, but the test substance may be administered orally or parenterally. Examples of the parenteral administration method include intravenous administration, subcutaneous administration, intradermal administration, intraperitoneal administration (ip), rectal administration, transdermal administration (coating) and the like.

A form of the test substance is not particularly limited, but the test substance can be used as a solid, a liquid, a mixture with a base, a suspension or a solution. In the case of the suspension or the solution, examples such as water, a pH buffer, a methylcellulose solution, a physiological saline, an aqueous organic solvent solution (as the organic solvent, ethanol and dimethyl sulfoxide are usually used) and the like are used. Examples of the base include oils such as glycerin, squalene and the like, and the base is used mainly for preparing a test substance for coating. A dose, an administration time and an administration term may be, for example, in such a range that they do not have severe effect on systemic condition, systemic various organs and tissues and the like (e.g. a dose is a maximum tolerance amount).

In the second step of the present searching method, the "symptom of a disease due to mood disorder or its related disorder, or an index value correlating therewith" can be assessed and measured, for example, by carrying out a behavioral analysis on a mammal to which a test substance is administered. The method of behavioral analysis can be specifically used by arbitrary selection among the aforementioned methods of behavioral analysis. For example, an isolation rearing test, a fear conditioning test, a defeat experience test, a forced swimming test and the like are preferably used. For example, it is preferable to select and use such a behavioral analysis method that a significant difference is detected between a mammal to which a positive control is administered, and a mammal to which a negative control is administered. After implementation of such the behavioral analysis method, in the third step and the fourth step of the present searching method, for example, a behavior is analyzed by comparing result obtained from a wild-type mammal to which a test substance is administered, and result obtained from a wild-type mammal to which a test substance is not administered (mammal which is to be a control of non-treatment). If the result of a wild-type mammal to which a test substance is administered is closer to the result of the present mammal than the result of a wild-type mammal to which a test substance is not administered (mammal which is to be a control of anon-treatment), it may be determined that the administered test substance is a substance which is an active ingredient of a medicament useful in treating mood disorder or its related disorder and, based on result of the determination, and a test substance may be selected. Herein, in place of the wild-type mammal to which a test substance is not administered, a wild-type mammal to which a negative control is administered may be used.

Examples of other method, when a test substance is administered to the present mammal or is contacted with the present mammal, include a method of measuring an expression level of the present gene as an "index value correlating with symptom of mode disorder or its related disorder" and the like. Examples of the index showing an expression level of the present gene include a transcript level of the present gene such as an RNA amount and the like, a translation product amount of the present gene such as a protein amount and the like, and the like. Specifically, an expression level of the present gene may be measured, for example, by a method of measuring a transcript amount of the present gene per specimen at a unit amount, a method of measuring a translation product amount of the present gene per specimen at a unit amount, or the like. Herein, the "specimen" includes a biological sample having a possibility that the present gene is contained, specifically, examples include a tissue such as a brain tissue and the like taken from the present mammal, or a cell separated from these tissues, or a cultured cell therefrom. These samples may be used as they are as a specimen, or a sample prepared from such the samples by various procedures such as separation, fractionation, immobilization and the like may be used as a specimen. Since a Gm1 protein is expressed particularly remarkably in a human brain, it is particularly preferable to utilize a brain tissue as the biological sample.

For measuring a transcription level of the present gene, for example, an amount of a mRNA which is a transcript of the gene is measured. The mRNA amount of a particular gene may be specifically measured, for example, by a quantitative real time-polymerase chain reaction (hereinafter, referred to as quantitative RT-PCR), a Northern hybridization method [Molecular Cloning 2nd edition authored by J. Sambrook, E. F. Frisch, T. Maniatis, published by Cold Spring Harbor Laboratory, 1989], a DNA array method, an in situ-hybridization method or the like.

In addition, for measuring a translation product amount of the present gene, for example, an amount of a protein having an amino acid sequence encoded by a nucleotide sequence of the present gene is measured. An amount of a particular protein can be specifically measured, for example, by an immunological measuring method using an antibody specific for the protein (e.g. ELISA, Western blotting, RIA, immunohistochemical test etc.), a two-dimensional electrophoresis method, high performance liquid chromatography or the like. The antibody specific for a protein having an amino acid sequence encoded by a nucleotide sequence of the present gene can be prepared using, as an immunological antigen, a protein having an amino acid sequence encoded by a nucleotide sequence of the present gene according to a conventional method.

A method of measuring a transcript amount of the present gene will be further explained.

An amount of a mRNA which is a transcript of the present gene can be measured, for example, by employing a probe or a primer designed and prepared based on a nucleotide sequence of the present gene, and using a conventional genetic engineering method, for example, a Northern hybridization method, quantitative RT-PCR, a DNA array method, an in situ-hybridization method or the like. Specifically, the measurement can be performed according to the method described, for example, in Northern hybridization method [Molecular Cloning 2nd edition authored by J. Sambrook, E. F. Frisch, T. Maniatis, published by Cold Spring Harbor Laboratory, 1989]. Thereupon, an amount of a mRNA such as a gene whose expression level in a tissue is known to be homeostatically constant (hereinafter, referred to as control gene), for example, a β-actin gene Nucl. Acids. Res., vol. 12, No. 3, p. 1687, 1984) and a 36B4 (Acidic Ribosomal Phosphoprotein) (Nucl. Acids. Res., vol. 19, No. 14, p. 3998, 1991) gene may be measured simultaneously. Then, by calculating a mRNA amount of the present gene or its index value per mRNA amount of a control gene or its index value, an expression level of the present gene may be obtained.

(1. Northern Hybridization Method)

First, a DNA of a gene for which a mRNA amount is to be measured is prepared and, then, a DNA consisting of all or a part of it is labeled to prepare a probe.

The above gene can be prepared by PCR employing, as a template, a commercially available cDNA (available from, for example, TAKARA SHUZO Co., Ltd.) or a cDNA prepared by the method shown below. For example, first, from a tissue expressing the gene, a total RNA is extracted by a conventional method such as a guanidine hydrochloride/phenol method, a SDS-phenol method, a guanidine thiocyanate/CsCl method and the like. For example, a total DNA may be extracted utilizing a commercially available kit such as ISOGEN (manufactured by Nippon Gene) and the like.

From the extracted total RNA, a mRNA is prepared, for example, as follows: First, a polyA column having oligo dT as a ligand is equilibrated using a 5-fold column volume or more of a Loading buffer [20 mM Tris hydrochloride buffer (pH 7.6), 0.5M NaCl, 1 mM EDTA, 0.1% (w/v) SDS], subsequently, the total RNA prepared by the above method is applied to a column, and the column is washed with a 10-fold column volume of a loading buffer. Further, the column is washed with a 5-fold column volume of a Washing buffer [20 mM Tris hydrochloride buffer (pH 7.6), 0.1M NaCl, 1 mM EDTA, 0.1% (w/v) SDS]. Subsequently, a mRNA is eluted with a 3-fold column volume of an elution buffer [10 mM Tris hydrochloride buffer (pH7.6), 0.1M NaCl, 1 mM EDTA, 0.05% (w/v) SDS] to obtain a mRNA.

Then, an oligo dT primer is annealed with a polyA chain of the total RNA or mRNA, and a single-stranded cDNA is synthesized according to a protocol, for example, of a cDNA synthesis kit (TAKARA SHUZO Co., Ltd.). Thereupon, an RNA used as a template may be either of a total RNA or a mRNA, and it is more preferable to use a mRNA.

By employing the single-stranded cDNA as a template, and using a DNA polymerase such as TaKaRa taq (TAKARA SHUZO Co., Ltd.), and the like, PCR is performed to amplify a DNA. PCR condition is different depending on a kind of an animal to be measured, a sequence of a primer used and the like, and examples include condition under which 30 to 55 cycles are performed in a reaction buffer [10 mM tris hydrochloride buffer (pH 8.3), 50 mM KCl, 1.5 mM $MgCl_2$] in the presence of 2.5 mM NTP, one cycle being incubation for 30 seconds at 94° C., 2 minutes at 40° C. to 60° C., and 2 minutes at 72° C.

The thus amplified DNA of the present gene may be cloned by inserting into a vector such as pUC118 and the like. A nucleotide sequence of the DNA can be confirmed by a Maxam Gilbert method (described in, for example, Maxam, A. M.&W. Gilbert, Proc. Natl. Acad. Sci., 74, 560, 1977 etc.) or a Sanger method (described in, for example, Sanger, F. & A. R. Coulson, J. Mol. Biol., 94, 441, 1975, Sanger, F, & Nicklen and A. R. Coulson., Proc. Natl. Acad. Sci., 74, 5463, 1977 etc.).

All or a part of the thus prepared DNA of the present gene is labeled with a radioactive isotope element or a fluorescent dye as follows, thereby, a probe can be prepared. As the probe, probes having a nucleotide number of usually 15 bp to a full sequence, having a nucleotide length of preferably 15 bp to 1 kb, more preferably 100 bp to 1 kb can be exemplified. For example, using the above-prepared DNA as a template, and using an oligonucleotide having a partial sequence of a nucleotide sequence of the DNA as the primer, PCR is performed by adding dNTP containing [$\alpha$-$^{32}$P]dCTP or [$\alpha$-$^{32}$P]dATP to a reaction solution, thereby, a probe labeled with $^{32}$P is obtained. Alternatively, the above-prepared DNA may be labeled using a commercially available labeling kit such as a Random prime labeling Kit (Boehringer Mannheim), MEGALABEL (TAKARA SHUZO Co., Ltd.) and the like.

Then, Northern hybridization analysis is performed using the above probe. Specifically, a total RNA or a mRNA is prepared from a tissue or a cell for which an expression level of the present gene is to be measured 20 μg of the prepared total RNA or 2 μg of the mRNA is separated by an agarose gel, the gel is washed with 10×SSC (1.5M Nacl, 0.35M sodium citrate), and the separated RNA is transferred to a nylon membrane [e.g. Hybond-N (manufactured by Amersham Biosciences Corp.)] from the gel. The membrane is placed into a polyethylene bag, 25 ml of a hybridization buffer [6×SSC (0.9M NaCl, 0.21M sodium citrate), and 5×Denhardt solution [0.1% (w/v) Ficoll 400, 0.1% (w/v) polyvinylpyrrolidone, 0.1% BSA], 0.1% (w/v) SDS, 100 μg/ml denatured salmon sperm DNA, 50% formamide] is added into the bag. After the bag is incubated at 50° C. for 2 hours, the hybridization buffer is discarded, and 2 ml to 6 ml of a hybridization buffer is newly added. Further, a labeling probe obtained by the aforementioned method is added, and this is incubated at 50° C. overnight. As a hybridization buffer, in addition to the aforementioned buffer, commercially available DIG easy Hyb (Roche Diagnostic) can be used. The membrane is removed, and incubated at room temperature for 15 minutes in 50 ml to 100 ml of 2×SSC containing 0.1% SDS, the same procedure is repeated once and, finally, the membrane is incubated at 68° C. for 30 minutes in 50 ml to 100 ml of 0.1×SSC containing 0.1% SDS. By measuring an amount of a label on the membrane, an amount of mRNA that is a transcription product of the present gene can be measured.

(2. Quantitative RT-PCR)

From a tissue or a cell for which an expression level of the present gene is to be measured, mRNA is prepared by the same method as that described in the (1 Northern hybridization method). To the prepared mRNA is added a reverse transcriptase such as MMLV (Toyobo Co. Ltd.) and the like, and a reaction is performed at 42° C. for 15 minutes to 1 hour in a reaction buffer [50 mM tris hydrochloride buffer (pH 8.3), 3 mM $MgCl_2$, 75 mM KCl, 10 mM DTT) in the presence of 0.5 mM dNTP and 25 μg/ml oligo dT, thereby, a corresponding cDNA is prepared. A corresponding cDNA may be prepared using a cDNA synthesis kit (TAKARA SHUZO Co., Ltd.). Employing the prepared cDNA as a template, and using an oligonucleotide having a part of a nucleotide sequence of the present gene as a primer, PCR is performed. Examples of the primer include primers comprising a partial nucleotide sequence of the present gene. Primers having a nucleotide length of usually 15 bp to 100 bp, preferably 15 bp to 50 bp, more preferably 15 bp to 35 bp can be exemplified. Examples of the PCR condition include the condition under which 35 to 55 cycles are performed in a reaction buffer [10 mM tris hydrochloride buffer (pH 8.3), 50 mM KCl, 1.5 mM $MgCl_2$] in the presence of 2.5 mM dNTP and [$\alpha$-$^{32}$P]-dCTP, one cycle being incubation for 30 seconds at 94° C., 2 minutes at 40° C. to 60° C., and 2 minutes at 72° C. The amplified DNA is subjected to polyacrylamide gel electrophoresis, and a radioactive amount of the separated DNA is measured, thereby, an amount of a mRNA of the present gene can be measured. Alternatively, using TAKARA taq (TAKARA SHUZO Co., Ltd), 50 µl of a reaction solution containing 25 µl of SYBR Green PCR Reagents PCR (ABI) in a reaction buffer [10 mM tris hydrochloride buffer (pH 8.3), 50 mM KCR 1.5 mM $MgCl_2$], and PCR is performed using ABI7700 (ABI) at the condition under which incubation is performed at 50° C. for 2 minutes and at 95° C. for 10 minutes, and 40 cycles are performed, one cycle being incubation for 15 seconds at 95° C. and 1 minute at 60° C.

By measuring fluorescence of the amplified DNA, an amount of mRNA of the present gene can be measured.

(3. DNA Array Analysis)

For measuring a transcript amount of the present gene, a DNA array based on the known technique, such as a macroarray prepared by spotting a cDNA of the present gene on a membrane filter such as a nylon membrane and the like, a microarray prepared by spotting a cDNA of the present gene on a slide glass or the like, a probe array prepared by immobilizing an oligonucleotide (usually, chain length of 18 to 25 mer) having a partial sequence of a nucleotide sequence of the present gene on a slide glass utilizing an optochemical reactions and the like can be utilized. These arrays can be prepared according to the method described, for example, in Genome Function Study Protocol, Experimental Medicine Extra Volume (published by Yodosha) and the like. Alternatively, Genechip commercially available from Affymetrix may be utilized.

One example of a method for measuring an amount of a transcript of the present gene using a DNA array will be shown below.

(3-1. Quantitation with a Microarray)

By a method similar to the method described in the (1) Northern hybridization method), mRNA is prepared from a tissue or cell for which expression level of the present gene is to be analyzed. A reverse transcriptase such as MMTV (Toyobo Co., Ltd.) is added to the prepared mRNA, to react them at 42° C. for 15 minutes to 1 hour in a reaction buffer [e.g. a solution containing 50 mM Tris-HCl buffer (pH 8.3), 3 mM $MgCl_2$, 75 mM KCl and 10 mM DTT] in the presence of 0.5 mM dNTP, [$\alpha$]$^{32}$P]-dCTP, and 25 µg/ml oligo dT, whereby, labeled cDNA is prepared. Thereupon, a cDNA synthesizing kit (Takara Bio Inc.) may be used. A DNA array prepared by spotting, on a membrane filter, DNA probes having separate nucleotide sequences each consistent with all or a part of a nucleotide sequence of a desired gene to be analyzed, the present gene or the present full length cDNA is placed in a polyethylene bag, 25 ml of a hybridization buffer [6×SSC (0.9M NaCl, 0.21M sodium citrate), 5×Denhardt solution [0.1% (w/v) Ficoll400, 0.1% (w/v) polyvinylpyrrolidone, 0.1% BSA, 0.1% (w/v) SDS. 100 µg/ml denatured salmon sperm DNA, 50% formamide] is added, this is incubated at 50° C. for 2 hours, the hybridization buffer is removed, and 2 ml to 6 ml of a hybridization buffer is newly added. Further, to this is added the aforementioned labeled cDNA, and this is incubated at 50° C. overnight. As a hybridization buffer, in addition to the aforementioned buffer, commercially available DIG EASY Hyb (Roche Diagnostic) may be used. After the hybridization, the DNA array is removed, immersed in 50 ml to 100 ml of 2×SSC containing 0.1% SDS, and incubated at room temperature for about 15 minutes. Further, the same procedure is repeated once and, finally, incubation is performed at 68° C. for 30 minutes in 50 ml to 100 ml of 0.1×SSC containing 0.1% SDS. Then, by measuring an amount of label on the DNA array, an amount of mRNA which is a transcript of the present gene, that is, an expression level of the present gene can be measured.

(3-2. Quantitation with a Microarray)

By a method similar to the method described in the (1 Northern hybridization method), mRNA is prepared from a tissue or cell for which an expression level of the present gene is to be analyzed. A reverse transcriptase such as MMTV (Toyobo Co., Ltd.) is added to the prepared mRNA, to react them at 42° C. for 15 minutes to 1 hour in a reaction buffer [e.g. a solution containing 50 mM Tris-HCl buffer (pH 8.3), 3 mM $MgCl_2$, 75 mM KCl and 10 mM DTT] in the presence of 0.5 mM DNTP, Cy3-dUTP (or Cy5-dUTP) and 25 µg/ml oligo dT. To the reaction solution is added an alkali buffer (e.g. a solution containing 1N NaOH, 20 mM EDTA), this is incubated at 65° C. for 10 minutes, and free Cy3 or Cy5 is removed using MicroconYM-30 and the like, thereby, fluorescently labeled DNA is prepared as a probe. The prepared probe is hybridized with a microarray by a method similar to the method described in the (3-1 Quantitation with DNA microarray). By measuring an amount of signal on the array with a scanner, an amount of mRNA which is a transcript of the present gene, that is, an expression level of the present gene can be measured.

(3-3. Quantitation with a Probe Array)

From a tissue or a cell for which an expression level of the present gene is to be measured, a mRNA is prepared by the same method as that described in the (1 Northern hybridization method). A cDNA is prepared from the prepared mRNA using, for example, a cDNA synthesis kit (GENSET). The prepared cDNA is biotin-labeled using, for example, a biotin-labeled CRNA synthesis kit (In Vitro Transcription) (Enzo), and purified with a ORNA cleanup and quantitation kit (In Vitro Transcription). The generated biotin-labeled DNA is fragmented with a Fragmentation buffer (200 mM Tris acetate (pH 8.1), 500 mM KOAc, 150 mM MgOAc). To this are added an internal standard substance Control Oligo B2 (manufactured by Amersham), 100×Control CRNA Cocktail, Herring sperm DNA (manufactured by Promega), Acetylated BSA (manufactured by Gibco-BRL), 2×MES Hybridization Buffer [200 mM MES, 2M [Na$^+$], 40 mM EDTA, 0.02% Tween20 (manufactured by Pierce), pH6.5 to 6.7] and DEPC-treated sterilized distilled water, thereby, a hybricocktail is prepared.

After a probe array [e.g. Genechip (manufactured by Affymetrix) etc.] filled with a 1×MES hybridization buffer is spun in a hybrioven at 45° C. and 60 rpm for 10 minutes, the 1×MES hybridization buffer is removed. Thereafter, to the probe array is added 200 µl of the hybricocktail, and this is spun in the hybrioven at 45° C. and 60 rpm for 16 hours (hybridization). Subsequently, the hybricocktail is removed, this is filled with Non-Stringent Wash Buffer [containing 6×SSPE [20×SSPE (manufactured by Nakarai tesk) is diluted], 0.01% Tween20, and 0.005% Antifoam 0-30 (Sigma)], the probe array is mounted at a predetermined position on GeneChip Fluidics Station 400 (manufactured by Affymetrix), and this is washed according to a protocol. Then, according to a staining protocol EuKGE-WS2 of MicroArray Suite (Affymetrix), the probe array is stained. By measuring a fluorescent luminance at 570 nm with HP GeneArray Scanner (manufactured by Affymetrix), an amount of a mRNA which is a transcript of the present gene, that is, an expression amount of the present gene can be measured.

(4. In Situ Hybridization Method)

Fundamentally, an in situ hybridization method comprises (1) fixation and embedding of a tissue, and preparation of a section, (2) preparation of a probe, and (3) detection by hybridization, and can be performed according to the method described, for example, in Heiles, H. et al., Biotechniques, 6, 978, 1988; Genetic Technology Handbook, Yodosha 278 1001; Cell Technology Handbook, Yodosha, 214, 1992; or Cell Technology Handbook, Yodosha, 222, 1992 except that RNA or DNA pre-labeled with radioactive or non-radioactive substance is used as a probe.

When a RNA probe is prepared, first, a desired gene to be analyzed and the present gene or a full length cDNA is obtained by a method similar to the method described in the (1 Northern hybridization method), and the DNA is inserted into a vector having SP6, T7 or T3 RNA polymerase promoter (e.g. Bluescript of Strategene, pGEM of Promega etc.), which is introduced into *Escherichia coli*, thereby, plasmid DNA is prepared. Then, the plasmid DNA is cut with restriction enzymes so that a sense (for negative control) RNA and an antisense (for hybridization) can be prepared. Using either of the plasmid DNA as a template, and using $\alpha$-$^{35}$S-UTP in the case of a radioactive label, or digoxigenine UTP or fluorescein-modified UTP in the case of a non-radioactive label as a substrate, RNA is labeled while it is synthesized, using SP6, T7 or T3 RNA polymerase. The labeled RNA is cut into a suitable size for hybridization by alkali hydrolysis, thereby, RNA pre-labeled with a radioactive or non-radioactive substance is prepared. As a kit based on these methods, for example, a RNA labeling kit (Amersham Biosciences Corp.) is commercially available for a radioactive label, and DIG RNA labeling kit (Roche Diagnostic) and RNA color kit (Amersham Biosciences Corp.) are commercially available for a non-radioactive label. In addition, when a DNA probe is prepared, for example, by incorporation of a radioactive nucleotide labeled with $^{32}$P, or a nucleotide labeled with biotin, digoxigenine or fluorescein by a nick translation method [Sambrook, J. et al. Molecular Cloning: A laboratory Manual 3rd edition, Cold Spring Harbor Laboratory Press (2001)], or a random priming [Feinberg, A. P., B. Vogelstein, Anal. Biochem., 132, 6 (1083), Feinberg, A. P., B. Vogelstein, Anal. Biochem., 137, 266 (1984)], DNA pre-labeled with a radioactive or non-radioactive substance is prepared. As a kit based on these methods, for example, a nick translation kit (Amersham Biosciences Corp.), and Random Prime Labeling Kit (Roche Diagnostic) are commercially available for a radioactive label, and DIG DNA labeling kit (Roche Diagnostic), and DNA color kit (Amersham Biosciences Corp.) are commercially available for a non-radioactive label.

Specifically, a tissue or a cell for which an expression level of the present gene is to be measured is fixed with paraformaldehyde or the like, embedded in paraffin or the likes and a thin strip is prepared, and is applied on a slide glass. Or, the tissue or the cell is embedded in an OCT compound, and frozen in liquid nitrogen or isopentane cooled with liquid nitrogen, and a strip is prepared, and applied on a slide glass. A slide specimen is obtained in this manner.

Then, in order to remove a substance which non-specifically reacts with a used probe in the tissue or the cell, the above-prepared slide glass strip is treated with proteinase K, and is acetylated. Then, hybridization is performed between the slide glass strip and the above-prepared probe. For example, the probe is heated at 90° C. for 3 minutes, diluted with a hybridization solution, the solution is added dropwise to the slide glass strip for which the treatment is completed, to cover a film, and this is incubated in a moisture-chamber at 45° C. for 16 hours, thereby, a hybrid is formed. After hybridization, a non-specifically adsorbed or unreacted probe is removed by washing or the like (when an RNA probe is used, an RNase treatment is also added). As a transcript amount, for example, by measuring a label amount on a slide glass strip, or by counting an area or a cell number at a part exhibiting radioisotope or fluorescent activity in a thin strip, an amount of a mRNA which is a transcript of the present gene or a corresponding value can be measured.

Then, a method of measuring a translation product amount of the present gene will be further explained.

When a solution containing the present protein as a biological sample is utilized, for example, the method can be implemented by reacting the present protein contained in the biological sample with an antibody to the present body, and measuring an amount of the present protein which can bind to the antibody.

An animal species from which the antibody to the present protein can be derived is not particularly limited, but usually, an antibody prepared by using an antigen derived from the same kind as that of the present mammal is used.

The antigen to the present protein is not particularly limited in its form, and may be a polyclonal antibody using the present protein as an immune antigen, or a monoclonal antibody.

The antigen can be prepared according to the conventional method (Current protocols in Molecular Biology edit. Ausubel et al. (1987) Publish. John Wiley and Sons. Section 11.12 to 11.13). Specifically, a polyclonal antibody to the present protein can be obtained from serum of an immunized animal according to a conventional method, by immunizing a non-human animal such as a rabbit and the like, for example, using the present protein which was expressed in *Escherichia coli* or the like and purified according to the conventional method, or using an oligopeptide having a partial amino acid sequence of any of the present proteins synthesized according to the conventional method. On the other hand, in the case of a monoclonal antibody, a non-human animal such as a mouse and the like is immunized with the present protein which was expressed in *Escherichia coli* or the like and purified according to the conventional method, or an oligopeptide having a partial amino acid sequence of these proteins. From a hybridoma cell prepared by cell-fusing the resulting spleen cell and a myeloma cell, an objective monoclonal antibody can be obtained (Current protocols in Molecular Biology edit. Ausubel et al. (1987) Publish. John Wiley and Sons. Section 11.4 to 11.11).

The present protein used in preparing an antibody can be obtained by a procedure of DNA cloning, construction of each plasmid, transfection of a host, culturing of a transformant and recovery of the present protein from the culture, based on sequence information of the present gene. These procedures can be performed according to the methods already known to a person skilled in the art, or the methods described in references (Molecular Cloning, T. Maniatis et al., CSH Laboratory (1983), DNA Cloning, DM. Glover, IRL PRESS (1985)). Specifically, a recombinant DNA (expression vector) which can express a gene encoding the present protein in a desired host cell is prepared, and this is introduced into a host cell to transform it. The transformant is cultured, and an objective protein is recovered from the resulting culture. Alternatively, the present protein may be prepared by a general chemical synthesis method (peptide synthesis) according to information of an amino acid sequence provided by the present invention. Specifically, a liquid phase synthesis method and a solid phase synthesis method described in "Fandament and Experiment of Peptide Synthesis" (authored by Nobuo Izumiya et al., Maruzen, published in 1987) can be used.

In the third step and the fourth step of the present searching method, a measured value of an expression level of the present gene in a specimen from a mammal to which a test substance is administered, or with which a test substance is contacted, or a part thereof is compared with a control value of an expression level of the gene and, based on a difference thereof, a test substance having the effect of improving symptom of a disease due to mood disorder or its related disorder in the specimen is selected.

The control value of an expression level of the present gene may be, for example, a value of an expression level of the gene in a cell in a normal tissue. Herein, the "normal tissue" means, for example, a tissue derived from an individual which has not been affected with a disease due to mood disorder or its related disorder, and has no family history of a disease due to mood disorder or its related disorder.

Such the control value may be obtained by measuring an expression level of the present gene in a cell in a normal tissue together with an expression level of the gene in a specimen, or may be obtained by separated measurement. Alternatively, an expression level of the present gene in a cell in a plurality of normal tissues is measured, and an average may be used as a control value.

For example, when a value of an expression level of the present gene in a cell of a normal tissue is used as a control value, and a measured value of an expression level of the present gene in a specimen is higher than the control value, it can be assessed that a test substance which was administered to d specimen or contacted with a specimen has the effect of improving symptom of a disease due to mood disorder or its related disorder.

Examples of the control value of an expression level of the present gene include a value of an expression level in a cell of a tissue with which a test substance is not contacted.

Such the control value may be obtained by measuring an expression level of the present gene in a cell of a tissue which is not contacted with a test substance together with an expression level of the gene in a cell of a tissue which is contacted with a test substance, or may be obtained by separate measurement. For example, a part of a tissue before contact with a test substance is taken, an expression level of the present gene is measured, and the resulting value may be used as a control value. Alternatively, an expression level of the present gene in a cell of a plurality of tissues which is not contacted with a test substance is measured, and an average may be used as the control value.

For example, when a measured value of an expression level of the present gene in a cell of a tissue which is contacted with a test substance is higher than a value of an expression level of the present gene in a cell of a tissue which is not contacted with a test substance, this means the effect of improving symptom of a disease due to mood disorder or its related disorder, by contact with the test substance, and it can be assessed that the test substance has the effect of improving symptom of a disease due to mood disorder or its disorder.

Examples of the control value of an expression level of the present gene include a value of an expression level in a cell of a tissue which is contacted with a control substance as a test substance. Examples of the "control substance" include a positive control and a negative control. The "positive control" represents an arbitrary substance having the effect of improving symptom of a disease due to mood disorder or its related disorder. In addition, examples of the "negative control" include a solvent contained in a test substance, a test system solution which is to be background, and the like.

Such the control value may be obtained by measuring an expression level of the present gene in a cell of a tissue which is contacted with a control substance together with an expression level of the gene in a cell of a tissue which is contacted with a test substance, or may be obtained by separate measurement. Alternatively, an expression level of the present gene in a cell of a plurality of tissues which is contacted with a control substance is measured, and an average may be used as a control value.

When a control substance is a negative control, if a measured value of an expression level of the present gene in a cell of a tissue which is contacted with a test substance is higher than a value of an expression level of the present gene in a cell of a tissue which is contacted with a control substance, it means the effect of improving symptom of a disease due to mood disorder or its related disorder, by contact with the test substance, and it can be assessed that the test substance has the effect of improving symptom of a disease due to mood disorder or its related disorder. On the other hand, if a measured value of an expression level of the present gene in a cell of a tissue which is contacted with a test substance is equal to or lower than a value of an expression level of the present gene in a cell of a tissue which is contacted with a control substance, it can be assessed that the test substance has no effect of improving symptom of a disease due to mood disorder or its related disorder.

In addition, when a control substance is a positive control, by comparing a measured value of an expression level of the present gene in a cell of a tissue which is contacted with a test substance with a value of an expression level of the present gene in a cell of a tissue which is contacted with a control substance, the effect of improving symptom of a disease due to mood disorder or its related disorder of the test substance may be assessed.

The present mammal or a part thereof can be utilized as an animal to which the "positive control" is administered, or with which the "positive control" is contacted, or a part thereof.

Examples of the present determination method include:

(A) a method of determining susceptibility of an individual of a mammal for mood disorder of its related disorder, comprising (1) a step of obtaining a protein sample from the individual, and (2) a step of measuring abundance of the present protein in the protein sample (i.e. present determination method 1), and (B) a method of determining susceptibility of an individual of a mammal for mood disorder or its related disorder, comprising (1) a step of obtaining a nucleic acid sample from the individual, and (2) a step of measuring a transcription level of the present gene in the nucleic acid sample, or a step of assaying a polymorphism type of the present gene in the nucleic acid sample (i.e. present determination method 2).

The present determination methods 1 and 2 include so-called gene diagnosis (e.g., including mRNA level diagnosis, genome level diagnosis etc.), for example, for determining susceptibility of an individual of a mammal for mood disorder or its related disorder, and relate to the technique having a step of assaying a polymorphism type of the present gene as a means to diagnose sensitivity of a disease due to mood disorder or its related disorder.

As the method, fundamentally, the same method as that described above may be used, specifically, by utilizing, for example, a hybridization method using a probe in which a DNA of the present gene is labeled with an enzyme such as horseradish peroxidase (HRP) and the like, a radioactive isotope element, a fluorescent substance, or a chemiluminescent substance, or a PCR method using a primer designed based on a nucleotide sequence of the DNA, a transcription amount of the present gene in a nucleic acid sample obtained from an individual may be measured.

EXAMPLES

The present invention will be explained in more detail below by way of Examples, but the present invention is not limited to these Examples.

Example 1

Construction of Expression Plasmid for Human Gm1 Protein

In order to express a human Gm1 protein in brain neurons, a plasmid was prepared, the plasmid containing DNA in which a nucleotide sequence encoding a human 5 ml protein was linked to the downstream of a brain-specific enolase (NSE) promoter.

That is, after a plasmid pCR-Gm1, which was described in Publication US2005/260595, was double-digested with EcoRV and SpeI, the DNA was applied to agarose gel electrophoresis, and then was purified and recovered using QIAquick Gel Extraction Kit (manufactured by QIAGEN). The recovered DNA was used as an insert DNA. pcDNA3.1 (manufactured by Invitrogen) which had been double-digested with EcoRV and XbaI was used as a vector, the insert DNA was ligated thereto using a ligase, thereby, a plasmid pcDNA-Gm1 was prepared.

After a plasmid pNSE containing a NSE promoter was double-digested with BamHI and HindIII, the DNA was applied to agarose gel electrophoresis. The DNA was purified and recovered using QIAquick Gel Extraction Kit (manufactured by QIAGEN). The recovered DNA, and the plasmid pcDNA-Gm1 which had been double-digested with BglII and HindIII were ligated using a ligase to prepare an expression plasmid pNSE-hGml.

Example 2

Introduction of Expression Plasmid into Fertilized Ovum

The Gm1 expression plasmid pNSE-hGm1 prepared in Example 1 was microinjected into a male pronucleus of a fertilized ovum at one cell stage of a C57/BL6N mouse. This fertilized ovum was transplanted into an oviduct of a female C57/BL6N mouse which had been mated with a male C57/BL6N mouse subjected to previous vasoligation to induce pseudopregnancy. Twenty days after transplantation, a newborn mouse was obtained by natural delivery. A tail of an offspring mouse 6 weeks after birth was cut to extract a genomic DNA by a conventional method. By performing PCR using primers Tg1 and Tg2 which can amplify DNA comprising a nucleotide sequence encoding human Gm1, and employing the extracted genomic DNA as a template, a transgenic mouse was selected. That is, a tail of a mouse six weeks after birth was incubated at 55° C. overnight in a lysis buffer (50 mM Tris-HCl, pH7.0, 100 mM NaCl, 20 mM EDTA, 1% SDS) containing proteinase K (150 µg/ml). This lysis solution was extracted with phenol once, extracted with phenol/chloroform once and, subsequently, extracted with chloroform once. After the extract was precipitated with isopropanol, the resulting precipitate was resuspended in 100 µl of ultrapure water. PCR was performed using, as a template, 1 µl of this resuspended genomic DNA, and using 10 µM of a forward primer Tg1 (5'-ATGCTGCGCGACCAGAAGCGCGACCT; (SEQ ID NO: 3), 10 µM of a reverse primer Tg2 (5'-AGTCAGTGATAGGGGCTATGCTCTT; SEQ ID NO: 4) and TOYOBO KOD Taq polymerase (TOYOBO). The resulting PCR product was applied to electrophoresis with 2% agarose gel. A mouse for which a band of about 290 bp was detected on the gel was identified as a transgenic mouse. The transgenic mouse was raised in a rearing chamber maintained at a room temperature of 23° C. a humidity of 55% t and light and dark for each 12 hours.

Example 3

Confirmation of Expression Level of Gm1 in Transgenic Mouse Expressing Gm1 Protein The transgenic mouse obtained in Example 2 and a wild-type mouse were raised until 6-week old in a rearing chamber maintained at room temperature of 23° C., a humidity of 55%, and light and dark for each 12 hours. These mice were sacrificed according to the conventional method, a brain tissue was isolated. To the brain hemisphere was added 1 ml of a Trizol reagent (Invitrogen), and this was homogenized with a homogenizer. The homogenized solution was retained at room temperature for 5 minutes, and 200 µl of chloroform was added thereto. The resulting mixture was sufficiently mixed by vortexing, and further retained at room temperature for 3 minutes. Thereby, this was centrifuged (10,000 rpm, 10 minutes) to obtain a supernatant, and the supernatant was recovered into a tube. To the recovered supernatant was added 0.5 ml of isopropanol, and this was centrifuged (10,000 rpm, 10 minutes) to precipitate RNA. The precipitated RNA was recovered, and was suspended in 50 µl of MilliQ. This suspended RNA solution was treated with DNAase, extracted with phenol/chloroform, and precipitated with ethanol. The resulting precipitate (RNA) was suspended in 50 µl of MilliQ. The RNA concentration in the resulting suspension was measured using a spectrophotometer. And, using 1 ng of the thus prepared RNA as a template, and using 10 µM of a reverse primer Tg2 (5'-AGTCAGTGATAGGGGCTATGCTCTT; SEQ ID NO: 4) and a Superscript II RNA reverse transcriptase (Invitrogen), reverse transcription was performed. Using 2 µl of this reverse transcription product as a template, and using 10 µM of a forward primer Tg1 (5'-ATGCTGCGCGACCAGAAGCGCGACCT; SEQ ID NO: 3), 10 µM of a reverse primer Tg2 (5'-AGTCAGTGATAGGGGCTATGCTCTT; SEQ ID NO: 4), and TOYOBO KOD Taq polymerase (TOYOBO), PCR was performed. After the resulting PCR product was applied to electrophoresis with 2% agarose gel, the gel was stained with ethidium bromide. A band detected by ethidium bromide staining was measured quantitatively using Tyhoon (Amersham). As compared with the wild-type mouse, expression level of Gm1 was about 2 to 5 times higher in the transgenic mouse obtained in Example 2.

Example 4

Isolation Rearing Test of Transgenic Mouse Expressing Human Gm1 Protein

The transgenic mice obtained by Example 2 were reared in isolation to stress. Emotionality under stress was observed, and behavioral analysis of stress resistance was carried out.

That is, transgenic mice were reared by separating into two groups of: isolation rearing in which one mouse was reared in one cage, and group rearing in which three mice were reared in one cage. During a rearing period, a feed-water bottle, a cage and a feeder were exchanged two times a week. Before and after exchange of a cage, a response to a bar presented before a nose, a response when the air was brown, resistance to capturing and handling, a response when a tail was held with a forceps, and vocalization were observed to assess emotionality. In the same way, wild-type mice derived from a litter were reared either in isolation or in group, and emotionality of the mice were assessed at the same time when behavioral analysis of emotionality was carried out for the transgenic mice.

Mouse emotionality was scored according to the following assessment criteria. When a sum of respective scores was 19 to 24, this was determined to be high-emotional, 11 to 18 was determined to be normally emotional, and 0 to 10 was determined to be low-emotional.

Emotionality Assessment Criteria
A. Response to Bar Presented Before Nose
0: No response
1: Concern for subject
2: Defending or escaping behavior against subject
3: Aggressive behavior such as biting
4: Violent aggressive behavior
B. Response when Air was Blown
0: No response
1; Only slight body movement
2: Startle response
3; Remarkable startle response is exhibited, but jumping is not exhibited.
4: Remarkable astonishing response is exhibited, and jumping is exhibited.
C. Resistance to Capturing and Handling
0: No resistance, remarkable muscle relaxation
1: Easy capturing and handling
2: Easy capturing and handling, but slight muscle tension
3 Presence of muscle tension, difficult capturing and handling
4: Extremely difficult capturing, remarkable muscle tension
D. Response when Tail was Held with Forceps
0: No response
1: Concern for subject
2: Defending or escaping behavior against subject
3: Aggressive behavior such as biting
4: Violent aggressive behavior
E. Vocalization During Test (A-D)
0: No cry
1: Cry some times
2: Violent cry Results are shown in FIG. 1. By a stress in isolation rearing, emotionality was reduced in the wild-type mouse, while emotionality retained the normal state in the transgenic mouse. From this, it was found out that overexpression of 5 ml in a brain is effective in improving symptom of a stress-related mental disease.

Example 5

Fear Conditioning Test of Transgenic Mouse Expressing Human Gm1 Protein

Using transgenic mice obtained in Example 2, a fear conditioning test which is widely used in behavioral analysis of the antianxiety effect is performed for behavioral analysis of resistance to anxiety.

That is, the transgenic mouse or a wild-type mouse is placed in a fear-condition measuring apparatus (ACTI METRICS) under the condition without an electric shock. On the following day, the transgenic mouse or the wild-type mouse is placed again in the fear-condition measuring apparatus, and freezing time during a 4 minutes is measured under the condition without electric shock. This is regarded as freezing time without fear conditioning. The transgenic mouse or the wild-type mouse is placed in the fear-condition measuring apparatus, and an electric shock for 4 minutes as fear conditioning is given. Thereupon, an current intensity is 0.2 mA, and a stimulation time is one second every 10 seconds. On the following day, mice are placed again in the fear-condition measuring apparatus, and freezing time during a 4 minutes is measured under the condition without electric shock.

Based on a difference in the measured freezing time between the transgenic mouse and the wild-type mouse, if "resistance to anxiety" which is reduced in the wild-type mouse due to anxiety caused by fear conditioning retains normal state in the transgenic mouse, it is confirmed that overexpression of Gm1 in a brain is effective in improving symptom of a stress-related mental disease.

Example 6

Defeat Experience Test of Transgenic Mouse Expressing Human Gm1 Protein

Behavioral analysis of resistance to anxiety or the depression state is carried out by performing a defeat experience test using transgenic mice obtained by Example 2.

That is, by performing the following procedure, the transgenic mouse or a wild-type mouse is made to experience defeat. One pair of 10-week old male and female resident mice are housed together for 5 weeks or longer. A female mouse and an offspring mouse are excluded from a pair of mice in which an offspring mouse was born during housing together. Any one of the transgenic mouse and a wild-type mouse is placed therein, and biting behavior of the resident mouse is observed. At 20 times biting, the transgenic mouse or the wild-type mouse is isolated from the resident mouse. Thereupon, a time until the resident mouse bits the transgenic mouse or the wild-type mouse 20 times is measured. This defeat experience procedure is performed once a day for consecutive 10 days.

Based on a difference in the measured time until bitten 20 times between the transgenic mouse and the wild-type mouse, if "resistance to anxiety or depression state" which is reduced in the wild-type mouse due to anxiety or depression state caused by defeat experience retains normal state in the transgenic mouse, it is confirmed that overexpression of Gm1 in a brain is effective in improving symptom of a stress-related mental disease.

Example 7

Forced Swimming Test of Transgenic Mouse Expressing Human Gm1 Protein

Using transgenic mice obtained by Example 2, behavioral analysis of resistance to depression state is carried out by performing a forced swimming test which is widely used in behavioral analysis of the anti-depression effect.

That is, the transgenic mouse or a wild-type mouse is transferred into a laboratory, and made to be acclimated in the environment of the laboratory at least for 1 hour. The transgenic mouse or the wild-type mouse is slowly placed into a cylindrical cylinder having a diameter of 20 cm, and a height of 27 cm in which water at 23° C. to 25° C. is filled to a depth of 10 cm. Behavior of the mouse for 6 minutes after placed into water is recorded in a video, and a freezing time is measured.

Based on a difference in the measured freezing time between the transgenic mouse and the wild-type mouse, if "resistance to depression state" which is reduced in the wild-type mouse by the depression state due to forced swimming retains the normal state in the transgenic mouse, it is confirmed that overexpression of Gm1 in a brain is effective in improving symptom of a stress-related mental disease.

INDUSTRIAL APPLICABILITY

The present invention can provide, for example, a method for improving symptom of "mood disorder or its related disorders" such as depression and anxiety. The present invention can also provide a method for searching a substance which is an active ingredient of a medicament useful for treating the "mood disorder or its related disorders", and a model mammal utilized in the method and the like.

Free Text in Sequence Listing
SEQ ID NO: 3
Designed oligonucleotide primer for PCR
SEQ ID NO: 4
Designed oligonucleotide primer for PCR

---

The invention claimed is:

1. A method of reducing a stress-induced emotional response in a mammal under emotional stress comprising increasing a Gm1 protein or a protein comprising the amino acid sequence of SEQ ID NO:1 in the brain of the mammal, wherein increasing said Gm1 protein or a protein comprising the amino acid sequence of SEQ ID NO:1 in the brain of said mammal reduces a stress-induced emotional response in said mammal under emotional stress.

2. A method of reducing a stress-induced emotional response in a mammal under emotional stress comprising increasing the expression of a gene encoding a Gm1 protein or a gene encoding a polypeptide comprising the amino acid sequence of SEQ ID NO:1 in the brain of the mammal, wherein increasing said expression of a gene encoding a Gm1 protein or a gene encoding a polypeptide comprising the amino acid sequence of SEQ ID NO:1 in the brain of said mammal reduces the stress-induced emotional response in said mammal under emotional stress.

* * * * *